United States Patent
Koehler

(10) Patent No.: US 10,207,129 B2
(45) Date of Patent: *Feb. 19, 2019

(54) FACE MASK SEAL FOR USE WITH RESPIRATOR DEVICES AND SURGICAL FACEMASKS, HAVING AN ANATOMICALLY DEFINED GEOMETRY CONFORMING TO CRITICAL FIT ZONES OF HUMAN FACIAL ANATOMY, AND CAPABLE OF BEING ACTIVELY CUSTOM FITTED TO THE USER'S FACE

(71) Applicant: Richard H. Koehler, Tisbury, MA (US)

(72) Inventor: Richard H. Koehler, Tisbury, MA (US)

(*) Notice: Subject to any disclaimer, the term of this patent is extended or adjusted under 35 U.S.C. 154(b) by 722 days.

This patent is subject to a terminal disclaimer.

(21) Appl. No.: 14/447,134

(22) Filed: Jul. 30, 2014

(65) Prior Publication Data

US 2015/0040910 A1  Feb. 12, 2015

Related U.S. Application Data

(60) Provisional application No. 61/863,844, filed on Aug. 8, 2013, provisional application No. 61/864,387, filed on Aug. 9, 2013.

(51) Int. Cl.
*A61M 16/06* (2006.01)
*A62B 23/02* (2006.01)
(Continued)

(52) U.S. Cl.
CPC ........ *A62B 23/025* (2013.01); *A41D 13/1138* (2013.01); *A61M 16/0605* (2014.02);
(Continued)

(58) Field of Classification Search
CPC .......... A41D 13/1138; A61M 16/0605; A61M 2016/0661; A61M 2205/75; A62B 18/02;
(Continued)

(56) References Cited

U.S. PATENT DOCUMENTS 3,363,311 A  1/1968  Jowers
3,613,678 A  10/1971  Mayhew
(Continued)

FOREIGN PATENT DOCUMENTS

EP  1285594  11/2009
WO  WO 00/20072  4/2000
(Continued)

OTHER PUBLICATIONS

International Search Report and Written Opinion dated Oct. 9, 2014 in related PCT Application No. PCT/US2014/048963.
(Continued)

*Primary Examiner* — Peter S Vasat
(74) *Attorney, Agent, or Firm* — Knobbe, Martens, Olson & Bear LLP

(57) ABSTRACT

The present disclosure is a face seal (FS) device for filtering face piece respirators (FFR) of all types, that corrects inner face seal leakage (FSIL) of particulate material that occurs due to well documented failures in FS designs of the prior art. The present disclosure differs from those of the prior art in having compensatory accentuations at locations along the entire 360 deg. FS inner perimeter that are based on specific details of facial human anatomy which are known to be sites of FSIL. The FS is also constructed of a heat activated thermoplastic copolymer that enables the device to be custom fitted to the user's face. Experimental data, confirmed with workplace protective factor (WPF) studies, show a 60-240 fold improved performance over FS designs of the prior art.

20 Claims, 21 Drawing Sheets

1 = Rhinion= Osseocartilaginous Junction= "Nasal Bridge"
2 = NasoMaxillary Ridge/Process
3 = Maxillary Zygomatic Ridge
4 = Zygomatic Process (forward ridge)
5 = Bucchal Wall Soft Tissue Structures
6 = Mandibular Ramus, Body, Inferior Rim(s)
7 = Submental Soft Tissues

(51) Int. Cl.
 *A41D 13/11* (2006.01)
 *A62B 18/02* (2006.01)
 *A62B 18/08* (2006.01)

(52) U.S. Cl.
 CPC ............ *A62B 18/02* (2013.01); *A62B 18/025* (2013.01); *A62B 18/08* (2013.01); *A62B 18/082* (2013.01); *A62B 18/084* (2013.01); *A62B 23/02* (2013.01); *A61M 2016/0661* (2013.01); *A61M 2205/75* (2013.01); *Y10T 156/1043* (2015.01)

(58) Field of Classification Search
 CPC ..... A62B 18/025; A62B 18/084; A62B 23/02; A62B 23/025; A62B 18/08; A62B 18/082; Y10T 156/1043
 See application file for complete search history.

(56) References Cited

U.S. PATENT DOCUMENTS

| | | | |
|---|---|---|---|
| 4,373,520 A | 2/1983 | Arbique | |
| 4,536,440 A | 8/1985 | Berg | |
| 4,739,755 A | 4/1988 | White | |
| 4,807,619 A | 2/1989 | Dyrud et al. | |
| 4,827,924 A | 5/1989 | Japuntich | |
| 4,873,972 A | 10/1989 | Magidson et al. | |
| 5,003,633 A | 4/1991 | Itoh | |
| 5,090,407 A | 2/1992 | Lesage et al. | |
| 5,307,796 A | 5/1994 | Kronzer et al. | |
| 5,383,438 A | 1/1995 | Blumenstock | |
| 5,419,318 A | 5/1995 | Tayebi | |
| 5,553,608 A | 9/1996 | Reese et al. | |
| 5,558,089 A | 9/1996 | Castiglione | |
| 5,673,690 A | 10/1997 | Tayebi et al. | |
| 5,765,556 A | 6/1998 | Brunson | |
| 5,823,188 A | 10/1998 | Harges, Jr. et al. | |
| 6,058,610 A | 5/2000 | Leang | |
| 6,102,040 A | 8/2000 | Tayebi et al. | |
| 6,125,849 A | 10/2000 | Williams et al. | |
| 6,196,223 B1 | 3/2001 | Belfer et al. | |
| 6,214,094 B1 | 4/2001 | Rousseau et al. | |
| 6,532,598 B1 | 3/2003 | Cardarelli | |
| D483,476 S | 12/2003 | Von Hollen et al. | |
| 6,805,124 B2 | 10/2004 | Japuntich et al. | |
| 6,923,182 B2 | 8/2005 | Angadjivand et al. | |
| 6,978,782 B2 | 12/2005 | Tayebi | |
| 7,044,126 B2 | 5/2006 | Gavriely | |
| D529,396 S | 10/2006 | Rebecca Whipple | |
| D659,822 S | 5/2012 | Matula et al. | |
| 8,171,933 B2 | 5/2012 | Xue et al. | |
| D675,888 S | 2/2013 | Cline et al. | |
| 8,381,727 B2 | 2/2013 | Matich | |
| D689,341 S | 9/2013 | Dooley et al. | |
| D689,603 S | 9/2013 | Stockmann | |
| 8,789,532 B2 | 7/2014 | Hansen | |
| D717,939 S | 11/2014 | Koehler | |
| 9,320,923 B2 | 4/2016 | Koehler | |
| 9,468,782 B2 * | 10/2016 | Koehler ............ | A61M 16/0605 |
| 2002/0185133 A1 | 12/2002 | Japuntich et al. | |
| 2003/0019496 A1 | 1/2003 | Kopacko | |
| 2003/0136410 A1 | 7/2003 | Matich | |
| 2005/0211251 A1 | 9/2005 | Henderson et al. | |
| 2006/0085883 A1 | 4/2006 | Tan et al. | |
| 2006/0096598 A1 | 5/2006 | Ho | |
| 2006/0118116 A1 | 6/2006 | Porat | |
| 2007/0039620 A1 | 2/2007 | Sustello | |
| 2007/0044802 A1 | 3/2007 | Horne et al. | |
| 2008/0023006 A1 | 1/2008 | Kalatoor | |
| 2008/0099022 A1 | 5/2008 | Gebrewold et al. | |
| 2009/0065006 A1 | 3/2009 | Patterson | |
| 2009/0283096 A1 | 11/2009 | Cerbini | |
| 2010/0006100 A1 | 1/2010 | Eifler | |
| 2011/0061656 A1 * | 3/2011 | Matich .................. | A62B 18/025 128/206.25 |
| 2011/0067700 A1 | 3/2011 | Spoo et al. | |
| 2011/0088698 A1 | 4/2011 | Barnett | |
| 2011/0108035 A1 | 5/2011 | Samaniego | |
| 2011/0126841 A1 | 6/2011 | Matula, Jr. | |
| 2012/0017911 A1 | 1/2012 | Choi et al. | |
| 2012/0247474 A1 | 10/2012 | Torbenson | |
| 2014/0326245 A1 | 11/2014 | Teng | |
| 2015/0157823 A1 * | 6/2015 | Eury, Jr. ............ | A61M 16/0611 128/205.25 |

FOREIGN PATENT DOCUMENTS

| | | | |
|---|---|---|---|
| WO | WO 2007/068044 A1 | 6/2007 | |
| WO | WO 2012/064152 A2 | 5/2012 | |

OTHER PUBLICATIONS

Amazon, Oct. 28, 2014, 3M P100 Particulate Respirator Mask #8293, http://www.amazon.com/3M-P100-Particulate-Respirator, pp. 1.

Amazon, Oct. 28, 2014, Moldex 2300N95 Disposable Particulate Respirator N95 Dust Mask, http://www.amazon.com/Moldex-2300N95-Disposable-Particulate_Respirator, pp. 1.

Walgreens, Oct. 28, 2014, 3M Particulate Respirator face mask, N95, R8511ES, http://www.walgreens.com/store/c/3m-particulate-respirator-face-mask-,-n95,-r8511es/ID=prod6152466-product, pp. 1.

* cited by examiner

1 = Rhinion= Osseocartilaginous Junction= "Nasal Bridge"
2 = NasoMaxillary Ridge/Process       3 = Maxillary Zygomatic Ridge
4= Zygomatic Process (forward ridge)  5 = Bucchal Wall Soft Tissues
6= Mandibular Ramus, Body, Inferior Rim(s) 7= Submental Soft Tissues 1 = Rhinion= Osseocartilaginous Junction= "Nasal Bridge"
2 = NasoMaxiliary Ridge/Process
3 = Maxillary Zygomatic Ridge
4= Zygomatic Process (forward ridge)
5= Bucchal Wall Soft Tissue Structures
6= Mandibular Ramus, Body, Inferior Rim(s)
7= Submental Soft Tissues

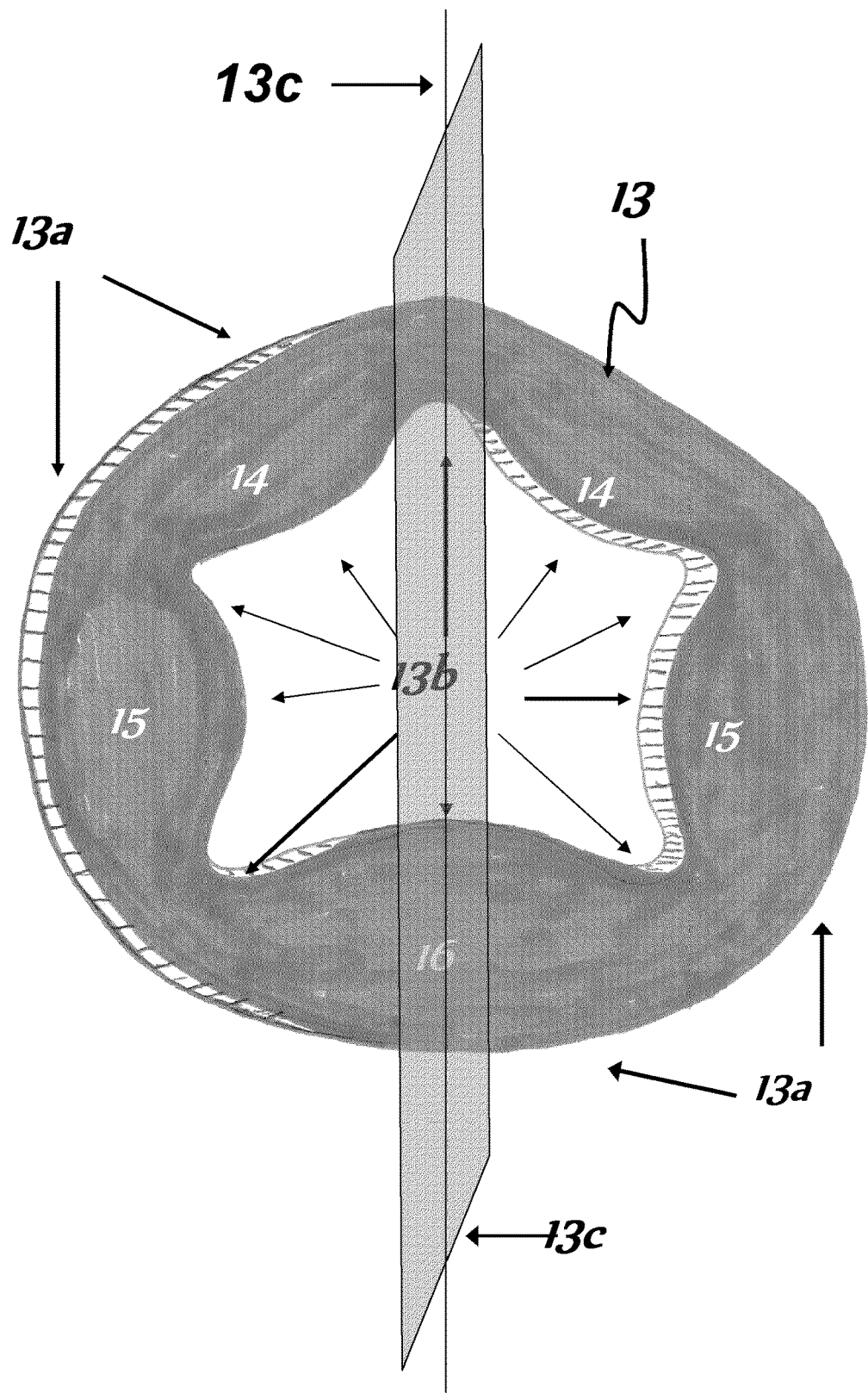

Heat Gun: 500Fdeg/ 2inches away/ 45-60 seconds/ constant motion around $360^0$ perimeter of seal *13*

*17*

*13*

Position mask *17* onto face, secure with straps and tighten to fit per OSHA protocol. Keep in place 2 minutes.

Test Chamber with
NaCl particle challenge

Fig. 13

| Mask # | Control | Mask/Test # | NON-HEATED | Mask # | HEATED |
|---|---|---|---|---|---|
| 1 | 11.1 | 2 | 3,697.5 | 3 | 1,354.9 |
| 4 | 116.0 | 8 | 6,241.9 | 6 | 1,778.0 |
| 7 | 116.0 | 11 | 9,831.3 | 9 | 2,847.9 |
| 10 | 651.5 | | | 12 | 1,310.8 |
| | | | | 13 | 1,475.3 |
| GM | 99.3 | GM: | 6,099.2 | GM: | 1,677.1 |
| GSD | 1.7 | | 1.2 | | 1.1 |

GM = Geometric Mean; GSD = Geometric Standard Deviation.
Control = (Control B) N100 Mask 17 with stock FS; NON-HEATED = N100 mask 17 with FS 13 3/8in unheated; HEATED = N100 Mask 17 with FS 13 3/8in heated as per protocol in Fig. 5.

GM = Geometric Mean; GSD = Geometric Standard Deviation; FFoverall = Overall Fit Factor. Control = (Control B) N100 Mask 17 with stock FS; Unheated 3/8 = N100 mask 17 with FS 13 3/8in unheated; Heated = Mask 17 with FS 13 3/8in heated as per Fig. 5 protocol.

Fig. 15

| Type | $FF^{[1]}_{normal}$ | $FF_{deep}$ | $FF_{side-side}$ | $FF_{up-down}$ | $FF_{talk}$ | $FF_{bend}$ | $FF^{[2]}_{normal}$ | $FF_{overall}$ |
|---|---|---|---|---|---|---|---|---|
| CONTROL | 4800 | 4460 | 1990 | 51 | 126 | 5 | 5 | 16 |
| CONTROL | 1410 | 4630 | 4510 | 35 | 329 | 26 | 285 | 93 |
| CONTROL | 3510 | 7360 | 10900 | 388 | 188 | 25 | 512 | 138 |
| UNHEATED 3/8 | 4890 | 3510 | 5360 | 4370 | 1030 | 1300 | 20100 | 2600 |
| UNHEATED 3/8 | 5230 | 4700 | 5720 | 6510 | 1630 | 3670 | 67900 | 4280 |
| UNHEATED 3/8 | 2500 | 7910 | 4940 | 7990 | 1880 | 5170 | 70600 | 4390 |
| HEATED 3/8 | 17600 | 2340 | 2550 | 1540 | 2190 | 1750 | 23400 | 2695 |
| HEATED 3/8 | 1980 | 2120 | 1090 | 6670 | 1150 | 2260 | 2930 | 1890 |
| HEATED 3/8 | 13800 | 9840 | 17200 | 13100 | 4460 | 7160 | 42700 | 10000 |

Control = N100 Mask B 17 with stock FS; UNHEATED 3/8 = N100 Mask 17 with FS 13 3/8in Unheated
HEATED 3/8 = N100 Mask 17 with FS 13 3/8in Heated as per protocol seen in Fig.5.

Fig. 16

| Subject | Test # | Control | Test # | NON-HEATED | Test # | HEATED |
|---|---|---|---|---|---|---|
| SG | 3 | 11.5 | 1 | 33,810 | 4 | 49,203 |
| SG | 7 | 618 | 2 | 6,494 | 6 | 7,573 |
| SG | 9 | 626 | 5 | 9,645 | 8 | 56,154 |
| RK | 11 | 1,442 | 10 | 6,970 | 12 | 4,584 |
| RK | 13 | 351 | 16 | 67,185 | 14 | 7,621 |
| RK | 15 | 27.4 | 18 | 25,703 | 17 | 9,935 |
| VA | 19 | 97.2 | 20 | 8,947 | 22 | 41,196 |
| VA | 25 | 35.6 | 21 | 60,732 | 23 | 112,502 |
| VA | 27 | 137 | 24 | 64,111 | 26 | 110,254 |
| | GM: | 145.6 | GM: | 21,262 | GM: | 24,923 |
| 3-subject averaging | GSD | 2.1 | | 1.5 | | 1.6 |

Control = Control B N100 mask 17 with stock FS;
NON-HEATED = Mask 17 with FS 13 3/8in. non-heated
HEATED = Mask 17 with FS 13 3/8in heated

*STATISTICAL ANALYSIS: p-value (threshold = 0.05)* vs.

| Control Mask B | ProtoType B-FS 13 | p-value |
|---|---|---|
| Control | NON-HEATED | 0.0036 |
| Control | HEATED | 0.0071 |
| NON-HEATED | HEATED | 0.4559 |

Control = Control B N100 mask 17 with stock FS;
NON-HEATED = Mask 17 with FS 13 3/8in. non-heated
HEATED = Mask 17 with FS 13 3/8in heated Example: test # 16, subject: RK, respirator model: non-heated Control = Control B N100 mask 17 with stock FS;
NON-HEATED = Mask 17 with FS 13 3/8in. non-heated
HEATED = Mask 17 with FS 13 3/8in heated

FACE MASK SEAL FOR USE WITH RESPIRATOR DEVICES AND SURGICAL FACEMASKS, HAVING AN ANATOMICALLY DEFINED GEOMETRY CONFORMING TO CRITICAL FIT ZONES OF HUMAN FACIAL ANATOMY, AND CAPABLE OF BEING ACTIVELY CUSTOM FITTED TO THE USER'S FACE

CROSS-REFERENCE TO RELATED APPLICATIONS

The present application claims priority to U.S. Provisional Application No. 61/863,844, filed on Aug. 8, 2013 and U.S. Provisional Application No. 61/864,387, filed on Aug. 9, 2013, each of which is herein incorporated by reference in its entirety.

BACKGROUND

Field

The present disclosure relates to the design of face seals (FS) for filtering facemask respirators (FFR), and specifically to minimizing FS inward leakage (FSIL) that occurs in FFRs.

The present disclosure also relates to the use of heat activated thermoplastic copolymers in the construction of a FS, and to critical areas of the human facial anatomy as they relate to FSIL.

Description of the Related Technology

Filtering face piece respirators (FFRs) play a critical role in everyday life. They are available for purchase to the general public in most hardware stores and are recommended, or required, for use in a wide variety of home, public, and occupational environments—especially in healthcare settings. Their principle function is to provide respiratory protection against both non-biological and biological particulate materials.

In practice, FFRs are used generally to protect the wearer. In healthcare institutions, and public health settings, however, FFRs must function both to protect the wearer from potentially harmful particulate matter, including biological pathogens, and/or to protect populations from a wearer exhaling such pathogens into the environment. During surgical procedures, for example, the smoke plume generated from electrosurgical use has been shown to contain a wide variety of vaporized viral organisms capable of infection, including HIV and Human Papilloma Virus (HPV). A FFR in such a setting must therefore protect the surgeon and those in the operating room, while at the same time protecting the patient from the surgeon's exhaled pathogens coming into contact with the surgical field. In certain public health settings, FFRs must be able to effectively protect the wearer and/or the surrounding human contacts from biological organisms in a wide range of sizes: from large bacteria at 0.300 to 1.0 micros, to the H7N7 and H7N9 Asian flu virion, where the particle size can be as small as 40-80 nanometers.

The design features of any FFR that provide its intended protection to the user are: 1) the filter element itself, and 2) the mechanism of sealing the mask to the wearer's face.

With respect to the filter materials in the FFR assembly: FFRs are certified by the National Institutes of Occupational Safety and Health's (NIOSH) approval regulation 42 CFR 84, to provide a variety of levels of protection. These NIOSH ratings range from having 95% efficiency at filtering non-oil based aerosolized particulate matter (N95), to 100% efficiency (P100) in filtering particulate matter that is oil-based where the filter itself must be strongly resistant to oil. Volatile organic compounds (VOCs) and other such vapor hazards require half face or full face elastomeric respirators with specific cartridge-based filters (OV/P100), which are commonly referred to as "gas masks".

At the other extreme are simple so-called "dust masks", and surgical masks. It should be noted that surgical masks are not FFRs and are not certified for use by the NIOSH. Likewise, so-called "N95 surgical mask respirators", while being NIOSH certified with respect to the "N95" rating, are not certified by the NIOSH for use in surgery. Instead, a surgical mask of any kind must pass the FDA's approval process which uses testing standards of the American Society of Testing and Materials (ASTM): F1862, F2100-11, and F2101-07.

For the FFR to provide the stated protection level to the user, it must pass the Occupational Safety and Health Administration's (OSHA) respirator standard 29 CFR 1910.134., Appendix A, Part 1: "Accepted Fit Test Protocols", Section A: "Fit Testing Procedures—General Requirements", pp. 1-13, which involves an initial "user seal test" to evaluation the FFR for obvious leaks around the edges of the mask.

A second, more specific fit testing may then be required: OSHA 29 CFR 1910.134., Appendix A, Part 1: "Accepted Fit Test Protocols", Section A: "Fit Testing Procedures—General Requirements", pp. 14A: "Test Exercises", subsec 1-8 and pp14B. This is performed with optical particle counters, and looks specifically at the actual particle concentrations outside and inside the mask while it is being worn. In essence, this is a test of how well the FS on the FFR performs in relationship to the filter rating of the FFR. This difference, depending on the experimental design and the filter rating, can represent the FFR's FSIL.

With respect to sealing the mask to the wearer's face, the principal reason to achieve such a seal is to avoid leakage around, rather than through, the filter portion of the mask. This is true for both inhaled and/or exhaled particulate matter coming from the user. There are two components involved: the straps that hold the mask to the face, and the FS itself.

NIOSH certification of FFRs has been a major advance in the development and classification of effective filters for FFRs. However there remains a significant problem with FSIL between the mask and the user's face. FSIL has been shown to occur in virtually all N95 FFRs and is dependent on multiple factors including: overall design of the FFR; FS design and the material used; the mechanism of attachment of the FFR to the wearer's face; and the particle sizes being filtered. Most reports conclude that the overwhelming factor in FFR FSIL is the FS component itself. That is, the filter elements themselves perform very well, if not exceeding the NIOSH certification standards. Yet if there is any degree of FS failure, the protection factor (PF) of the FFR can drop significantly: the reduction of protection due to FSIL in some N95 FFRs has been shown to be up to a 90% failure to filter out sub-micron size aerosolized particles. This is true for particle sizes less than 0.300 μm, which includes many viruses in the size ranges of 40-120 nanometers, in particular the Swine flu and Avian flu viruses.

FSIL creates a unique problem for healthcare workers in operating room settings on two fronts:

The first is that a smoke plume is generated during the customary widespread use of electrocautery during surgical procedures. OSHA estimates that 500,000 workers are exposed to laser and electrocautery smoke each year. Electrocautery creates particles with the smallest mean aerodynamic size of 0.07 μm—far smaller than the filtering capability of a N95 FFR. Studies have shown that a range of aerosolized toxins are present, including multiple volatile organic compounds that are either known, or suspected, carcinogens. Intact strands of human papillomavirus DNA have been isolated from carbon dioxide laser plumes during treatment of plantar warts and recurrent respiratory papillomatosis. Viable bacteriophage have also been demonstrated to be present in laser plumes. Whole intact virions have been found and their infectivity demonstrated. HIV DNA has been identified in laser smoke, and has also been shown to be capable of transmitting infections into cultured cells.

As far back as 1981 there were opinions being stated as to the need for new standards for protective masks in the operating room environment (see: "Proposed Recommended Practice for OR Wearing Apparel, AORN JOURNAL, v. 33, n. 1, pp. 100-104, 101 .1981"). The AORN has also published a Position Paper on the hazards of surgical smoke for several years, calling for " . . . high filtration surgical masks (to be) worn properly".

It is recognized that the inhalation dangers in surgical settings are compounded by the non-use of N95 respirators in all but those procedures involving HPV containing lesions—such as in the laser removal of genital warts. In the vast majority of surgical procedures, during which extremely high levels of particulate material are generated into the smoke plume, there is no requirement for N95 FFRs to be worn. Many investigators now agree that the protection provided by surgical masks may be insufficient in environments containing potentially hazardous sub-micron-sized aerosols.

However, even if N95 FFRs were to be required in operating rooms to protect the user from the wide range of harmful particles in surgical smoke, the FSIL failures of such FFRs will result in significant reductions of the expected protection afforded to the user.

The second problem unique to the operating environment is the shedding of potentially infectious bacteria onto the surgical field. A vast majority of surgical masks in use today are of a comparatively loose fitting nature and do not generally have a tightly sealed facial border. Typically such masks are manufactured from a variety of molded layered fibrous filtration materials designed for one-time disposable usage. U.S. Pat. No. 3,613,678 (Mayhew), U.S. Pat. No. 5,307,796 (Kronzer), U.S. Pat. No. 4,807,619 (Dyrud) and U.S. Pat. No. 4,536,440 (Berg) are all examples of the prior art. These features of surgical masks have raised concerns about the limitations of surgical masks, dating as far back as 1941, and continuing to the present day as to the effectiveness of such masks in preventing infections in surgical patients. Studies have confirmed that passage of inspired air around the periphery of two types of face masks appears to circumvent the mask's ability to screen airborne contaminants. Similar studies have revealed that Gram-positive staphylococci bacteria—a highly common cause of surgical site infections (SSI), were frequently isolated from air samples obtained throughout the operating room, including areas adjacent to the operative field. Nasopharyngeal shedding from persons participating in the operation was identified as the source of many of these airborne contaminants. Failure of the traditional surgical mask to prevent microbial shedding is likely associated with an increased risk of perioperative contamination. These deficiencies take on considerable importance with respect to the costs, both physical and economic, of surgical site SSIs. A 2009 high profile report by the CDC's Division of Healthcare Quality Promotion estimated that there were 290,485 SSI's per year in US hospitals—16% of all hospital acquired infections, second only to urinary catheter related infections. With an estimated average cost of $17,500 per patient, these SSI's cost upwards of $22 million dollars per year.

Given the previously discussed FSIL issues with all FFRs, in relation to the sizes of inhaled pathogens, and the sizes of exhaled pathogens, it is accurate to conclude that even the addition of N95 surgical mask respirators in the operating room will be unlikely to have a significant impact on the shedding of potentially harmful organisms from exhalations vapors of surgical personnel into the surgical field.

There have been many ongoing efforts by those of skill in the art to address the well-documented issue of FSIL in FFRs, and in surgical masks. The most basic design feature used to achieve some degree of a tight fit to the wearer's face has been to design the mask body, both in surgical masks and in FFRs, to be generally cup-shaped, and to have some form of a shaping layer where the inner mask perimeter has some slight curvature of the region from the nasal bridge itself down on to the sides of the nose. Simple face masks, including surgical face masks, as well as FFRs have utilized this design concept extensively. U.S. Pat. No. 3,613,678 (Mayhew), U.S. Pat. No. 5,307,796 (Kronzer), U.S. Pat. No. 4,807,619 (Dyrud), U.S. Pat. No. 4,536,440 (Berg), U.S. Pat. No. 4,873,972 (Magidson), U.S. Pat. No. 4,827,924 A5 (Japuntich), and U.S. Pat. No. 6,923,182 (Angadjivand) are just a few such examples that are well known to those reasonably skilled in the prior art.

Another very common design, in an effort to improve the FS at the nasal bridge section, is to include a malleable nose clip or bar that is secured on the outer face of the mask body centrally adjacent to its upper edge to enable the mask to be deformed or shaped in this region in order to obtain a better fit along what is commonly referred to as the "bridge" of the nose. Such nose bars, or clips, are well known to those reasonably skilled in the prior art.

A nose clip is described in U.S. Pat. No. 5,558,089 (Castiglione), Pat. App. 2011/0067700 (Spoo) and U.S. Pat. No. 5,307,796 (Kronzer). These are just a few such examples of the prior art.

Such nose clips are also commonly associated with a strip of foam affixed to the length of the clip, typically made from materials of either polystyrene, polyester, or neoprene. Examples of such foam strips are described in U.S. Pat. No. 5,765,556 (Brunson), and U.S. Pat. App. 2005/0211251 (Henderson).

Another design feature on FSs of the prior art, to improve the FS fit at the nasal bridge section, is to add some varying degree of asymmetric outward extension to make the foam strip wider at the sides of the nasal bridge. One such example is U.S. Pat. No. 8,171,933 (Xue) which describes a preformed nose clip that follows a general curve off the nasal bridge to the sides, exerting a force resiliently inward on each side of the wearer's nose when the mask is worn. This feature is claimed to eliminate the need for the wearer to individually shape the nose clip to the wearer's face. Another such example is U.S. Pat. 2008/0023006 (Kalatoor) which also describes a mask body where at least the first major surface of the nose foam has a predetermined concave curvature, which is claimed to have less opportunity to become pinched or unnecessarily deformed before being placed on wearer's face. These examples differ substantially from the present disclosure in that: the foam strip in these examples only involves the nasal portion of the FS perimeter; it has no inward convex protrusions to address the rest of the entire FS perimeter; and in that it does not involve any specific anatomically defined inner perimeter convex accentuations of the FS that conform specifically to the critical fit zones (CFZs) of the human face as described herein, and as will be further described in the illustrations below of the present disclosure.

Another such example is U.S. Pat. App. 2008/0099022 (Gebrewold), which describes a respiratory mask that has a nose foam that has a particular preconfigured shape for assisting in providing a snug fit over the wearer's nose. The nose foam has a nose-contacting surface that is skewed at first and second angles to a plane that extends to the nose foam. It is also claimed that the fit may be able to be achieved without use of a nose clip. However, this device differs substantially from the present disclosure in that the design feature described does not address the entire 360 degrees of the FS perimeter, and in that it does not involve any other specific anatomically defined inner perimeter convex accentuations of the FS that conform specifically to the CFZs of the human face as described herein, and as further described in the illustrations below of the present disclosure.

Another design feature to improve the FS fit is to include a vapor seal either across the top portion of the mask to assist in preventing fogging of the mask, or around the entire perimeter of the mask. U.S. Pat. No. 5,383,438 (Raines) is an example of such a design feature, as is U.S. Pat. No. 5,553,608 (Reese), which describes a stretchable material around the mask. Such a feature is well known to those reasonably skilled in the prior art. These features differ substantially from the present disclosure in that the FS design in these examples has no specific anatomically defined inner perimeter convex accentuations that conform specifically to the CFZs of the human face as described herein, and as further described in the illustrations below of the present disclosure.

Another design feature of face masks and FFRs of the prior art, in order to improve the FS fit to the user's face, is to utilize different materials than other such masks of the prior art. One such example is U.S. Pat. App. 2007/0039620 (Sustello), which uses an expandable or compressible material, such as a viscoelastic foam, or other such materials with similar characteristics, to enhance a seal between the mask and a user's face in an area extending over the bridge of the nose and generally under the eyes. However this represents a thin layer of viscoelastic material across the nasal section only, and is primarily intended to minimize fogging of a user's glasses or goggles due to warm humid exhalation vapors that, in fact, escape the FS due to FSIL in the device itself. Unlike the present disclosure, the feature described also doesn't involve any specific anatomically defined inner perimeter convex accentuations that conform specifically to the CFZs of the human face as described herein, and as further described in the illustrations below of the present disclosure.

Another example is U.S. Pat. App. 2012/0017911 (Choi), which describes a mask housing that is made entirely of a closed cell foam layer that has a plurality of fluid permeable openings located therein. The closed cell foam shaping layer is claimed to provide a sufficient degree of pliability at the perimeter, and is also claimed to enable the mask body to fit comfortably and snugly on a wearer's face without attachment or use of an elastomeric face seal, nose foam, or nose clip. However, unlike the present disclosure, this device does not involve any specific anatomically defined inner perimeter convex accentuations of the FS that conform specifically to the CFZs of the human face as described herein, and as further described in the illustrations below of the present disclosure.

Some existing FFRs use some form of an adhesive to attach the face seal directly to the user's face. U.S. Pat. No. 6,125,849 (Williams) is one such example. Another such example is U.S. Pat. No. 8,381,727 (Matich), which describes a mask with a FS comprised of an endless skin adhesive seal on the inside of the covering, with multiple such adhesive seals applied to each other and the inside of the mask shell perimeter. The authors provide examples of fit factors (FFs) determined by scientific measuring protocols and methods that are well to known to those reasonably skilled in the prior art. The results showed overall FF improvements of 20-80 percent when the seal was applied to industry standard N95 FFRs, versus the same FFRs with their stock FSs. Some individual FFs were over 300 in "experienced users", and as high as 1170. However, the use of N95 FFRs for such experimental studies can be considered problematic. This is due to the fact that for a given N95 FFR, a 5% total IL can be expected. Thus if one is trying to compare two FSs for only their FSIL component of the total IL on a given N95 FFR, then the IL measured cannot entirely be distinguished as only FSIL versus trans-filter leakage through the N95 FFR's filter element.

There have also been concerns about comfort issues with adhesives, applied directly to the face, being removed on a regular basis as would be required in many healthcare settings, particularly in surgical settings.

FSIL is difficult to reduce because of the significant variances in human facial anatomy. Anthropometric studies have revealed the substantial differences in the multiple variables of human facial anatomy. These are notable, perhaps not coincidentally, in the three areas that are common for FSILs to occur: 1) the nasal bridge and the cheek bone, 2) the cheek bone to the edge of the lower jaw, and 3) around and under the area between the undersurface of the chin back toward the angle of the jaw. The problem of FSIL may also be compounded by FFRs being made in fairly generic "small, medium, and large" sizes, and often simply as a "one size fits all" design. Therefore it can be seen that for existing FFRs:

That FSIL is a major problem that impairs critical protection by up 90%

That FSIL is due almost completely to failure of the FS itself

That FSIL occurs in specific areas where a FS contacts the human face

That multiple studies by multiple individuals and institutions of skill in the art have shown that existing FS designs do not compensate for all such known anatomic areas that correspond to such areas of FSIL.

There is therefore a need to redesign FFR FSs to decrease, or even eliminate FSIL. The present disclosure achieves this, by addressing all of the above factors, and represents an entirely new concept in FS design. The present disclosure's design is based on:

specifically defined CFZs identified in human facial anatomy that correspond to the known areas of FSIL the specific compensations for these areas in the geometric design of the FS that correspond to the CFZs involved in FSIL the thermally-activated heat-fitting characteristic of the material used in the FS, such that the FS can be actively fitted to the user's face Testing results at the laboratory level, and confirmed in studies of both Simulated Workplace Protective Factor (SWPF) and Work Place Protective Factor (WPF) settings, performed with N100 FFRs to eliminate the filter element itself as a factor in FSIL, have shown that the level of FSIL reduction provided by this presently disclosed apparatus represents a highly significant improvement in FS and FFR technology. The protection factors measured are 60-240 times higher than FFR FSs of the prior art, and the geometric means (GMs) of the WPFs were over 21,000.

SUMMARY OF CERTAIN INVENTIVE ASPECTS

The present disclosure provides a face seal for use in face masks and filtering face piece respirators (FFRs) of all types, that is comprised of: (a) a geometric design based upon specifically defined critical fit zones (CFZs) identified in human facial anatomy that correspond to the known areas of face seal inward leakage (FSIL) that occur in virtually all such face masks and FFRs of the prior art, and which are identified at: (i) the area bordered by the Rhinion-Osseocartilaginous Junction ("Nasal Bridge"), along the NasoMaxiliary Ridge/Process, the Maxillary Zygomatic Ridge, and on to the Zygomatic Process forward ridge ("cheek bone") that comprises CFZ-I; (ii) the area from the Zygomatic Process forward ridge ("cheek bone"), along the Bucchal Wall Soft Tissue Structures and on to the Mandibular Ramus, Body, Inferior Rim that comprises CFZ-II; and (iii) the area from the Mandibular Ramus, Body, Inferior Rim on one side of the face across to the other side's Mandibular Ramus, Body, Inferior Rim, and the Submental Soft Tissues in the zone between these areas, that comprises CFZ-III; and (b) an inner perimeter geometric design with specific convex and/or concave accentuations that are designed specifically to compensate for the corresponding specific anatomic features of the human face involved in the Critical Fit Zones I thru III above; and (c) being composed of a thermoplastic copolymer material that can be actively fitted to the user's face.

The present disclosure differs substantially from those face seals of the prior art in that all of the areas of human facial anatomy, and of face seal designs of the prior art that are known to be involved in FSIL, have been addressed individually and specifically with unique design features in both the geometry of, and the material composition of, the present disclosure.

Testing results, at the laboratory level, and confirmed in studies of both Simulated Workplace Protective Factor (SWPF) and Work Place Protective Factor (WPF) settings, performed with N100 FFRs to eliminate the filter element itself as a factor in FSIL, have shown that the level of FSIL reduction provided by this apparatus represents a highly significant improvement over those face seals of the prior art. The protection factors measured are 60-240 times higher than FFR face seals of the prior art.

These and other advantages of the present disclosure are more fully demonstrated in the illustrations and detailed descriptions. Various embodiments may take on other modifications and alterations without departing from the spirit or scope of the disclosure as described in the illustrations above. Accordingly, this disclosure is not to be limited to the above described illustrations, but rather by the limitations set forth in the following claims and any equivalents thereof provided.

GLOSSARY

The descriptive terminology used herein shall have the meanings as set forth below, unless indicated otherwise:

"accentuation, accentuated, accentuated for" means to have or make convex and/or concave changes on the shape of the inner perimeter of the face seal embodiments herein described, to achieve the compensatory features described above.

"compensate(s) for, compensatory, compensated for" all mean to be designed to minor-image the specific area(s) of the facial anatomy that correspond(s) to, and therefore come in contact with, the described areas of the face seal embodiments herein described.

"concave" means an inward projection, with respect to the inner perimeter of a face seal, away from the inside center of the face seal.

"convex" means an outward projection of the face seal, with respect to the inner perimeter of a face seal, toward the inside center of the face seal.

"corresponding accentuations" means areas along the inner perimeter of the face seal embodiments herein described, that mirror-image the specific areas of the facial anatomy herein described that will come in contact to, and hence fit into, these specific areas along the inner perimeter of the face seal embodiments herein described.

"Critical Fit Zone I": the area bordered by the Rhinion-Osseocartilaginous Junction, or "Nasal Bridge" along the NasoMaxiliary Ridge/Process, the Maxillary Zygomatic Ridge, and on to the Zygomatic Process (forward ridge "cheek bone").

"Critical Fit Zone II": the area starting at the Zygomatic Process, along the Bucchal Wall Soft Tissue Structures and on to the Mandibular Ramus, Body, Inferior Rim.

"Critical Fit Zone III": the area starting at the Mandibular Ramus, Body, Inferior Rim, along the area on both sides of the under surface of the face, and the Submental Soft Tissues across to the opposite Mandibular Ramus, Body, Inferior Rim.

"Experimental Laboratory": means a testing setup and method in an artificially controlled environment.

"FF": means a Fit Factor as determined by experimental protocols consistent with those as described in OSHA Respirator Standard, 29 CFR 1910.134.

"FFoverall": means a computation based on FFs during each of 8 fit test exercises consistent with those as described in OSHA Respirator Standard 29 CFR 1910.134.

"FFR": means a filtering facepiece respirator.

"FM": means face mask.

"Face Mask Perimeter": means any or all points of contact between any aspect of a FM, a FFR, a half face mask elastomeric respirator, or a full face mask elastomeric respirator, and the corresponding surfaces of the human face.

"FS": means a seal, or an area intended to function as a seal, on a FM, a FFR, a half face mask elastomeric respirator, or a full face mask elastomeric respirator, that is intended to prevent inhaled and/or exhaled particulate matter, or gaseous vapors, from leaking between the perimeter edges of such masks or respirators, and the corresponding surfaces of the human face that said perimeter edges come in contact with, which thereby allows said particulate matter, or gaseous vapors, to bypass the filtering elements of said masks or respirators.

"FSIL": means leakage of inhaled and/or exhaled particulate matter, or gaseous vapors, from outside of a FM, a FFR, a half face mask elastomeric respirator, or a full face mask elastomeric respirator, being worn by a user, to the inside of the said mask or respirator, between the perimeter edge of such mask or respirator—where said perimeter edge is intended to function as the FS on said mask or respirator, and the corresponding surfaces of the human face to which said perimeter edge comes in contact with in any way, resulting in said particulate matter, or gaseous vapors, bypassing the said mask or respirator's filter element.

"GM": means Geometric Mean.

"GSD": means Geometric Standard Deviation.

"Heated": means a version of the FS composed of a material, or materials, that is designed to be thermally activated in order to be custom-fitted to the user's face, and is being used in its thermally activated state.

"Herein": means as being referred to anywhere in the text, illustrations, and/or tables of this report in any of its forms now, or in the future.

"IL": means the total amount of leakage of inhaled and/or exhaled particulate matter, or gaseous vapors, from outside of a FM, a FFR, a half face mask elastomeric respirator, or a full face mask elastomeric respirator, being worn by a user, to the inside of said mask or respirator, resulting in said particulate matter, or gaseous vapors, bypassing the said mask or respirator's filter elements.

"Not Heated": means a version of the FS composed of a material, or materials, that is designed to be thermally activated in order to be custom-fitted to the user's face, and is being used in its non-thermally activated state.

"Prototype": means any N100 FFR herein described with its stock FS removed and replaced with embodiments herein described.

"Report": means the work presented herein and in its entirety.

"Stock": means the form of the device as it is made commercially, or otherwise, available.

"SWPF": means Simulated Workplace Protection factor, which has an FFoverall based on studies performed in an environment designed to equal as closely as possible the conditions that would be encountered in the work place setting where the intended use of the FFR would take place.

"WPF": means Workplace Protective Factor, which has an FFoverall based on studies performed in the actual environment where the intended use of the FFR would take place.

BRIEF DESCRIPTION OF THE DRAWINGS

Features of the present disclosure will become more fully apparent from the following description and appended claims, taken in conjunction with the accompanying drawings. It will be understood these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Certain Inventive Embodiments" one will understand how illustrated features serve to explain certain principles of the present disclosure.

FIG. 3A demonstrates a plane of bisection 13c longitudinally through the FS 13

FIG. 13 is a chart depicting numerical results of SWPF studies.

FIG. 15 is a chart depicting the results of SWPF studies for individual face seal masks.

FIG. 16 is a chart depicting individual mask's GMs and GSDs.

DETAILED DESCRIPTION OF CERTAIN INVENTIVE EMBODIMENTS

Figure 1:
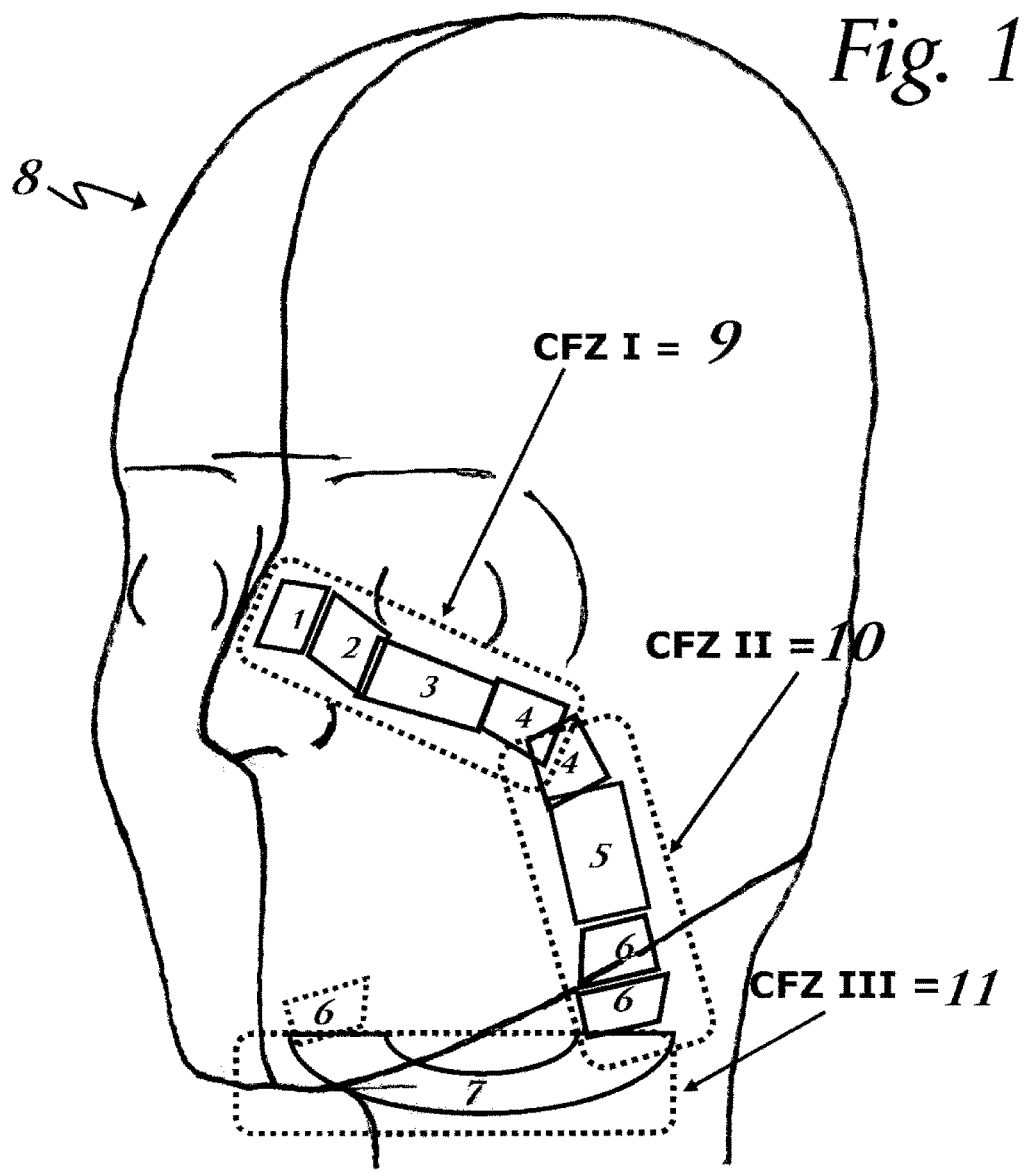
FIG. 1 demonstrates the herein defined Critical Fit Zones, CFZ-I, CFZ-II & CFZ-III, labeled as 9, 10, 11, and as defined by human facial anatomy 8.

FIG. 1 illustrates the three Critical Fit Zones (CFZs), of the human face involved in FSIL and as defined herein by: "CFZ-1" 9 being the area bordered by the Rhinion-Osseo-cartilaginous Junction, or "Nasal Bridge" 1, along the Naso-Maxillary Ridge/Process 2, the Maxillary Zygomatic Ridge 3, and on to the Zygomatic Process (forward ridge "cheek bone") 4; "CFZ-2" 10 being the area from the Zygomatic Process (forward ridge "cheek bone") 4 along the Bucchal Wall Soft Tissue Structures 5 and on to the Mandibular Ramus, Body, Inferior Rim 6; and; "CFZ-3" 11 being the area from the Mandibular Ramus, Body, Inferior Rim 6 on one side of the face, and the Submental Soft Tissues 7 in the zone from one portion of the inferior rim 6 across to the Mandibular Ramus, Body, Inferior Rim 6 on the opposite side of the face. It should be noted that anthropometric studies of the human facial anatomy have documented in detail the extensive differences in all regions of the face, and in particular the dimensions that are involved in the regions that correspond to the CFZs 9, 10, 11 above and sited elsewhere herein. Data from multiple studies have revealed that for any given face with any given face mask, FSIL occurs at one or more of locations 9, 10, and 11 specifically. The present geometric configuration of one embodiment of a FS 13 represents a departure from those devices of the prior art in having specific substantial compensatory convex accentuations of the inner perimeter of 13 at points 14, 15, 16 corresponding to CFZs 9, 10, 11 respectively.

Figure 2:
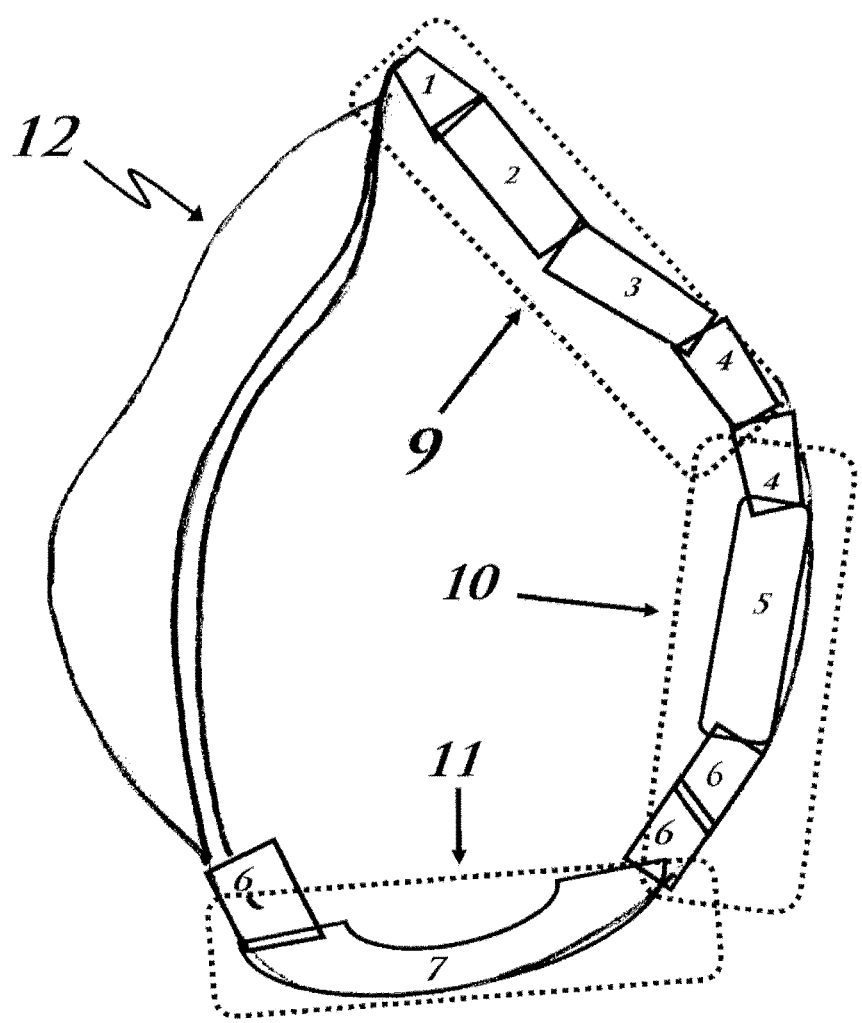
FIG. 2 demonstrates the inner aspect of a typical cup shaped FM or FFR shell 12, with inner surfaces that correspond to CFZ areas 9, 10, 11.

FIG. 2 illustrates the view of the inside of a typical face mask 12 of the prior art. Each of the CFZs 9, 10, 11 corresponding to anatomic components 1, 2, 3, 4, 5, 6, 7 is illustrated as it relates to the corresponding regions along the inside perimeter of the mask shell 12.

Figure 3:
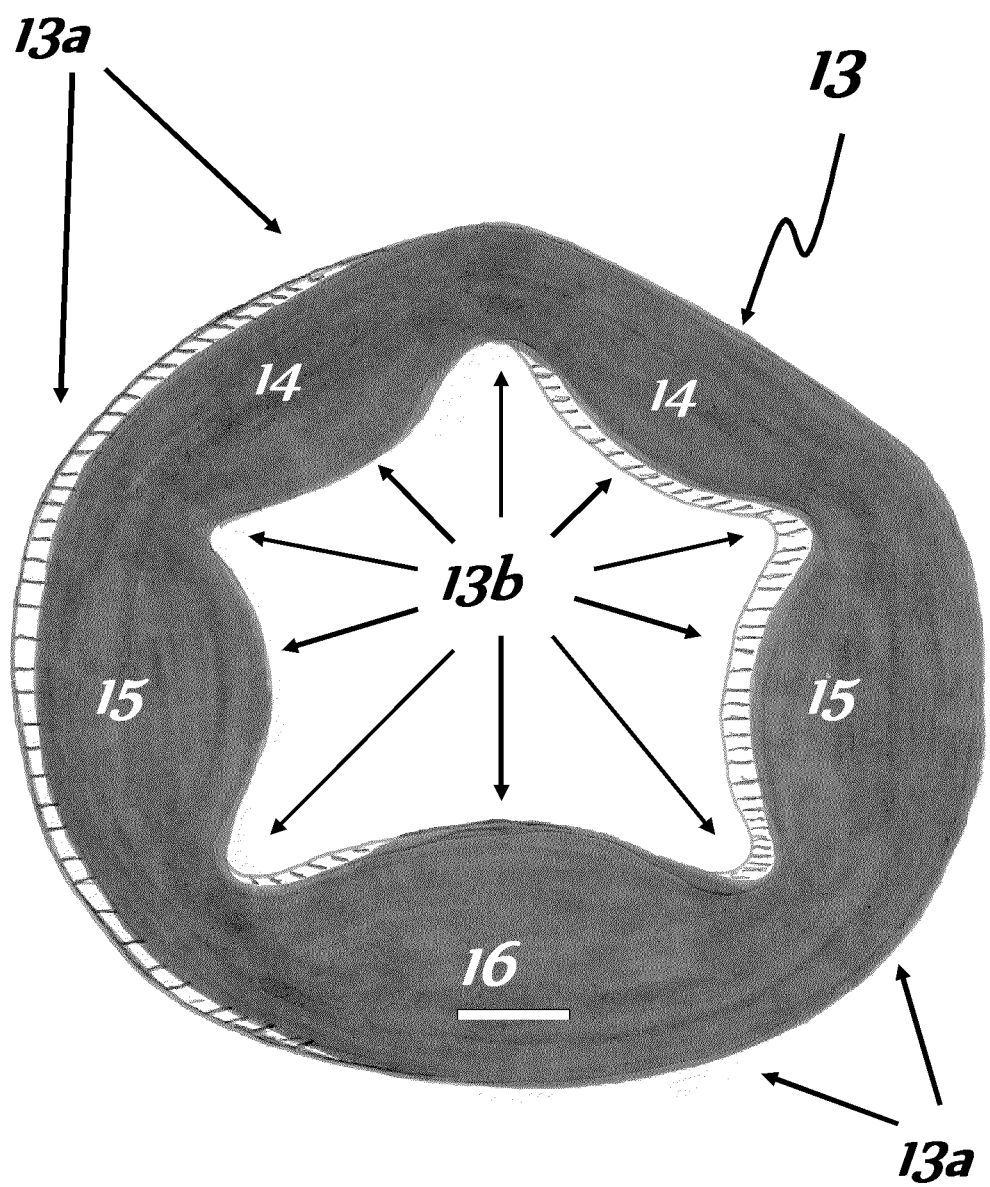
FIG. 3 demonstrates a complete free standing form of one embodiment of a FS 13 in straight on view with anatomic areas 9, 10, 11 compensated for by the corresponding convex curved accentuations 14, 15, 16.

FIG. 3 illustrates one embodiment of a FS 13. CFZs 9, 10, 11 have each been compensated for by specific and substantial corresponding convex accentuations 14, 15, 16 along the inner perimeter 13b of FS 13. Each accentuation involves a convex curved reciprocal portion that extends into the corresponding CFZ zone 9, 10, 11 of the human face that will come in contact with the FS 13 upon wearing of the mask 12. The region of 9 has been shown in anthropometric studies to be the shortest perimeter section of the three CFZ regions 9, 10, 11, and also possessing the deepest concavity of CFZs 9, 10, 11. Region 14 of FS 13 is correspondingly the shortest, and has the most convex accentuation, of regions 14, 15, 16 of the FS 13. Likewise, CFZs 10 and 11 are known to be similar in length and depth along the human face, although there is a slightly greater distance involved in CFZ 11 than in CFZ 10. Therefore the corresponding areas 14, 15, 16 of the FS 13 herein are designed to be compensating for these slight differences.

In some embodiments of the FS 13, these areas 14, 15, 16 may be further modified to conform to, compensate and reciprocate for, the CFZs 9, 10, 11 above. In some embodiments, there may be additional anatomically defined corresponding accentuations of the FS 13 at points other than, or in addition to, areas 14, 15, 16.

In some embodiments of the FS 13, the areas 14, 15, 16 may be custom-configured to the user's facial features comprised within CFZs 9, 10, 11 by being cut from an image guided, computer generated pattern that is unique to the user's face. In some embodiments, there may be additional anatomically defined corresponding accentuations of the FS 13 at points other than, or in addition to, areas 14, 15, 16 that may be custom-configured to the user's facial features comprised within CFZs 9, 10, 11 by being cut from an image guided, computer generated pattern that is unique to the user's face. It should be noted that any methodology of custom cutting the FS 13 and yielding areas 14, 15, 16 corresponding to CFZs 9, 10, 11 can be utilized to yield the FS 13 as described above.

In some embodiments of FS 13 the material used may be thermoplastic copolymer foam. One such thermoplastic copolymer foam may be ethylene vinyl acetate (EVA). However many such thermoplastic copolymer foams are applicable and well known to those familiar with the prior state of the art. In some embodiments of FS 13 the material used may be a solid thermoplastic copolymer. One such solid thermoplastic copolymer may be ethylene vinyl acetate (EVA). However many such solid thermoplastic copolymers are applicable and are well known to those familiar with the prior state of the art.

In some embodiments of FS 13 the material used may be heat activated thermoplastic copolymer foam which can be actively molded to a user's face. One such heat activated thermoplastic copolymer foam may be ethylene vinyl acetate (EVA). However many such heat activated thermoplastic copolymer foams are applicable and well known to those familiar with the prior state of the art.

In some embodiments of FS 13 the material used may be a solid heat activated thermoplastic copolymer. One such solid heat activated thermoplastic copolymer may be ethylene vinyl acetate (EVA). However many such solid heat activated thermoplastic copolymers are applicable and are well known to those familiar with the prior state of the art. In some embodiments of FS 13 the material used may pressure activated. In some embodiments of FS 13 the material used may be cold activated. In some embodiments of FS 13 the material used may be a viscoelastic copolymer foam. In some embodiments of FS 13 the material used may be solid viscoelastic copolymer. In some embodiments of FS 13, the thickness of the material may be anywhere from $1/16$ inch up to $1/2$ inch. It should be noted that any thickness of the FS 13 material can be utilized in so far as it allows for the same, or similar, performances in the testing results as discussed further herein.

FIG. 3A illustrates a hypothetical longitudinal plane of bisection 13c through FS 13.

Figure 3B:
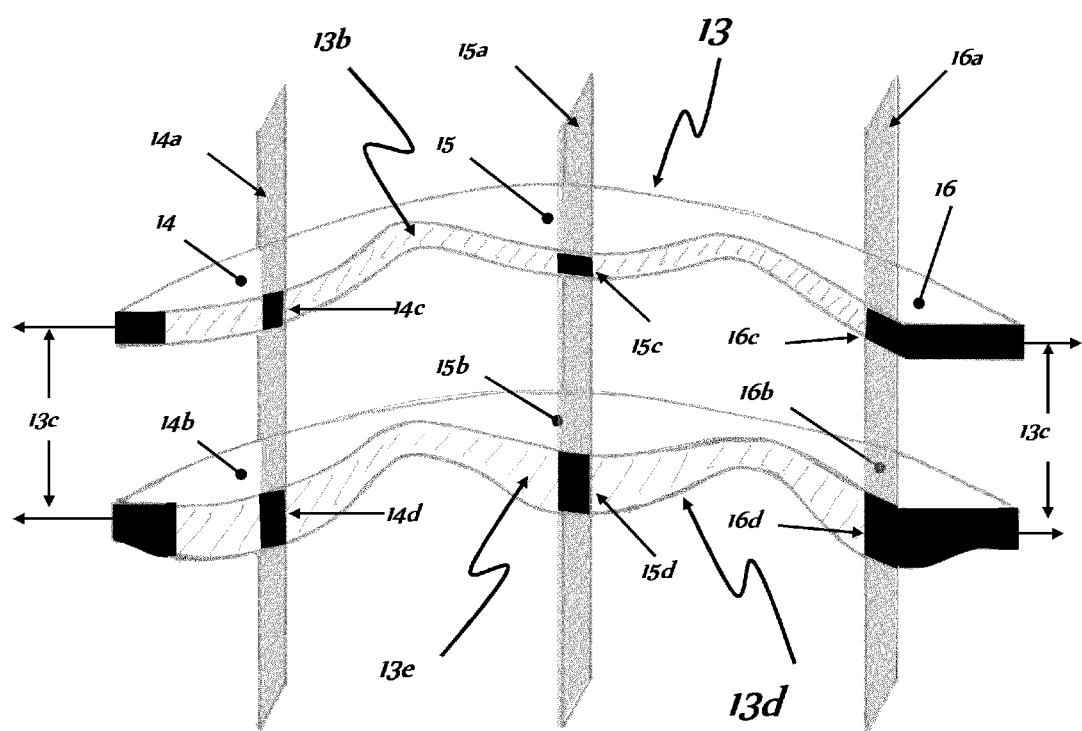
FIG. 3B demonstrates a horizontal cross sectional view of FS 13 at the point of the bisection plane 13c, in line with the same cross sectional view of a FS 13d with further accentuations of the perimeter 13b of FS 13 represented by new perimeter 13e of FS 13d. Both FS 13 and FS 13d have the same three parallel points of transection demonstrated by vertical planes 14a, 15a, 16a at the maximum convex accentuations of areas 14, 15, 16 and areas 14b, 15b, 15b respectively.

FIG. 3B illustrates a horizontal cross sectional view of FS 13 and an example of a different version of the FS 13 which is herein shown as FS 13d. The cross sectional view of both FS 13 and FS 13d is at the point of bisection plane 13c as illustrated in FIG. 3A above. Both FS 13 and FS 13d have the same three parallel points of transection demonstrated by vertical planes 14a, 15a, 16a at the maximum convex accentuations of areas 14, 15, 16 and areas 14b, 15b, 15b respectively. It can be seen that both FS 13 and FS 13d have identical convex accentuations of their respective inner perimeters 13b and 13e respectively, at locations indicated at 14, 15, 16 and 14b, 15b, 16b respectively. The thickness of inner perimeter 13b of FS 13 at points 14c, 15c, 16c can be seen as equal to each other, and equal to the rest of the perimeter 13b of FS 13. In contrast to FS 13, FS 13d has in the same three longitudinal planes of bisection, additional accentuations along perimeter 13e of FS 13d, at points 14d, 15d, 16d that are perpendicular to the areas 14b, 15b, 16b.

In some embodiments of the FS 13d example herein, the additional perpendicular accentuations along perimeter 13e of FS 13d, at points 14d, 15d, 16d may be seen as an increased thickness of the inner perimeter 13e at these locations versus the thickness of the rest of the inner perimeter 13e of FS 13d. In some embodiments, example version FS 13d may be made additionally thicker at areas 14b, 15b, 16b, along inner perimeter 13e, by adding further convex accentuations that are perpendicular to the axis of 13e, which are seen at points 14d, 15d, 16d along the inside perimeter 13e, of FS 13d.

In some embodiments, areas 14d, 15d, 16d of inner perimeter 13e may be thinner than the rest of the perimeter 13e.

In some embodiments, there can be further individual accentuations of example version FS 13d at any number of perimeter points 14d, 15d, 16d that may differ from the corresponding areas 14c, 15c, 16c of the inner perimeter 13b of FS 13.

Exemplary embodiments FS 13 and version FS 13d, illustrated in FIG. 3, FIG. 3A and FIG. 3B, are not intended to be the only such possible examples. It will be apparent to those skilled in the art that numerous such configurations of the inner perimeter 13b of FS 13 may be designed, and thereby that these illustrations may take on other modifications and alterations without departing from its spirit and scope of the disclosure as described in the illustrations above. Accordingly, these embodiments are not to be limited to the above described illustrations, but rather by the limitations set forth in the claims that follow.

Figure 4:
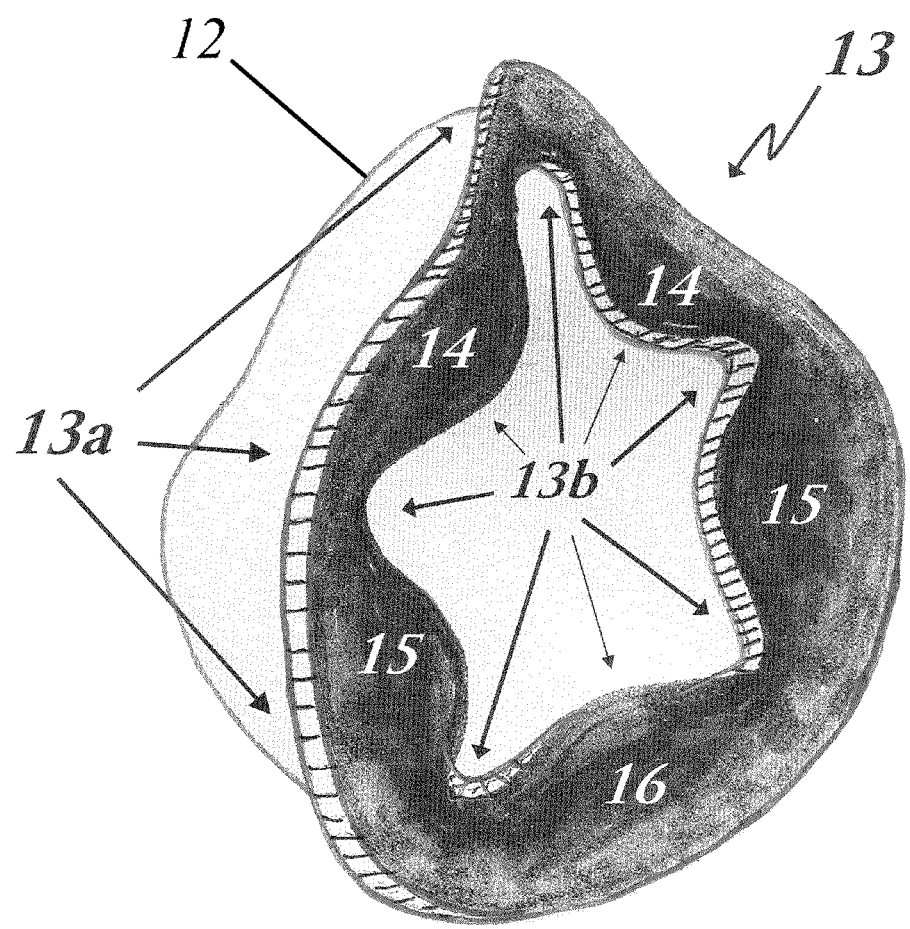
FIG. 4 demonstrates one embodiment of a FS 13 applied to the inside of the mask shell 12.

FIG. 4 illustrates the FS 13 described in FIG. 3 affixed to mask 12, being a typical cup shaped FFR of the variety that are well known to those familiar with the present state of the art. In some embodiments of FS 13, the mask 12 design may be of a rectangular configuration. In some embodiments, the mask 12 design may be of a generalized facial form fitting configuration. It should be noted that the outer perimeter 13a of FS 13 can be configured to be affixed to the corresponding outer perimeter of any such FFR known to those familiar with the present state of the art. In some embodiments of the FS 13, the entire FS 13 may be incorporated into the construction of the body of the mask 12. It should be noted that the FS 13 can be configured to be incorporated into either the corresponding outer perimeter of, or the body of, any such FFR known to those familiar with the present state of the art.

In some embodiments, FS 13 can be affixed to, or incorporated into the design of, a mask 12 which may be of a half mask respirator design. In some embodiments, FS 13 can be affixed to, or incorporated into the design of, a mask 12 which may be of a full mask respirator design. In some embodiments, FS 13 can be affixed to, or incorporated into, any form of device that is intended to either protect and/or cover part or all of the human face. Such applications for the FS 13 can include face goggles for skiing, aquatic sports face goggles, motorcycle goggles, aviation face goggles, military respirators, and first responder respirators. It should be noted that this list is not intended to be all-inclusive.

Figure 5A:
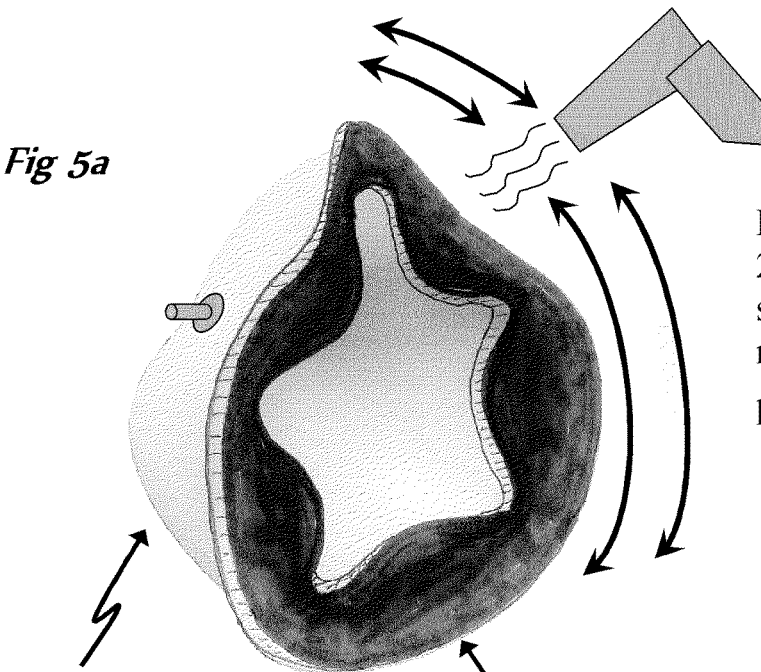
FIG. 5 demonstrates the protocol for heat activation of an embodiment of a FS 13 attached to N100 FFR mask 17, and subsequent fitting onto the user's face.

FIG. 5 illustrates the method used to achieve heat-activation of the FS 13 in all studies presented herein. In all studies presented herein, fixation of the FS 13 to N100 mask 17 was done with a heat-resistant silicon based adhesive (TW Permatex Inc., Solon, Ohio). Twelve hours were allowed for drying time of FS 13 to mask 17. Just prior to use, a standard heat gun (Ryobo Mod. HG600, One World Technologies, Inc., Anderson, Ohio) was used at set temperature of 500 Fdeg. In some embodiments, the temperature of the heat source can be less than about 100° F., about 100° F., 200° F., 300° F., 400° F., 500° F., or greater, or any temperature therebetween. The gun was held at a distance of 2 in from the surface face of FS 13. Using constant motion around the surface face of FS 13, the heating was carried out for approximately 2 minutes (FIG. 5a). In the case of the EVA foam, a distinct transition in the surface appearance occurred from that of a flat back to having a glossier black characteristic. In some embodiments, the distance of the heat source from the surface of FS 13 can be less than about 1 inch, 1 inch, 2 inches, 3 inches, 4 inches, 5 inches, 6 inches, 1 foot, 2 feet, or more, or any distance therebetween. The time for applying the heat may be less than about 30 seconds, about 1 minute, 1.5 minutes, 2 minutes, 3 minutes, 4 minutes, 5 minutes, or more, or any time therebetween. In some embodiments, the FS 13 can be heated to less than about 50° F., 60° F., 70° F., 80° F., 90° F., 100° F., 110° F., 120° F., or more, or any temperature therebetween.

Figure 5B:
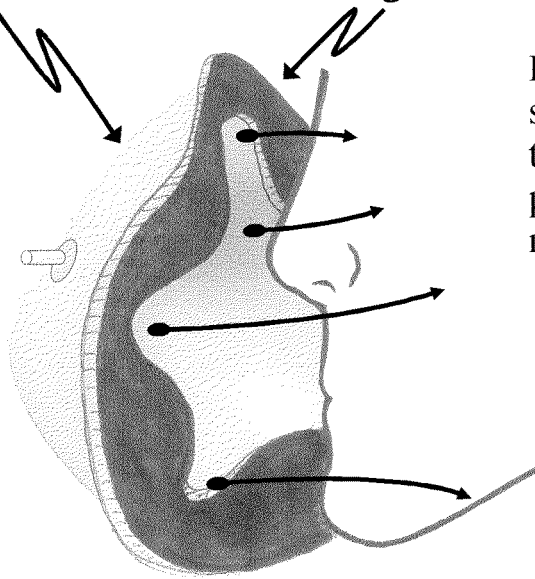

The mask 17 with FS 13 was then positioned on the user's face, by the user, and the holding straps were adjusted to obtain a secure fit, in compliance with OSHA's to 29CFR1910.134: Part I. OSHA-Accepted Fit Test Protocols; Appendix A, pp. 1-13. (FIG. 5b). After 90 seconds of cooling time, testing was begun.

Figure 6:
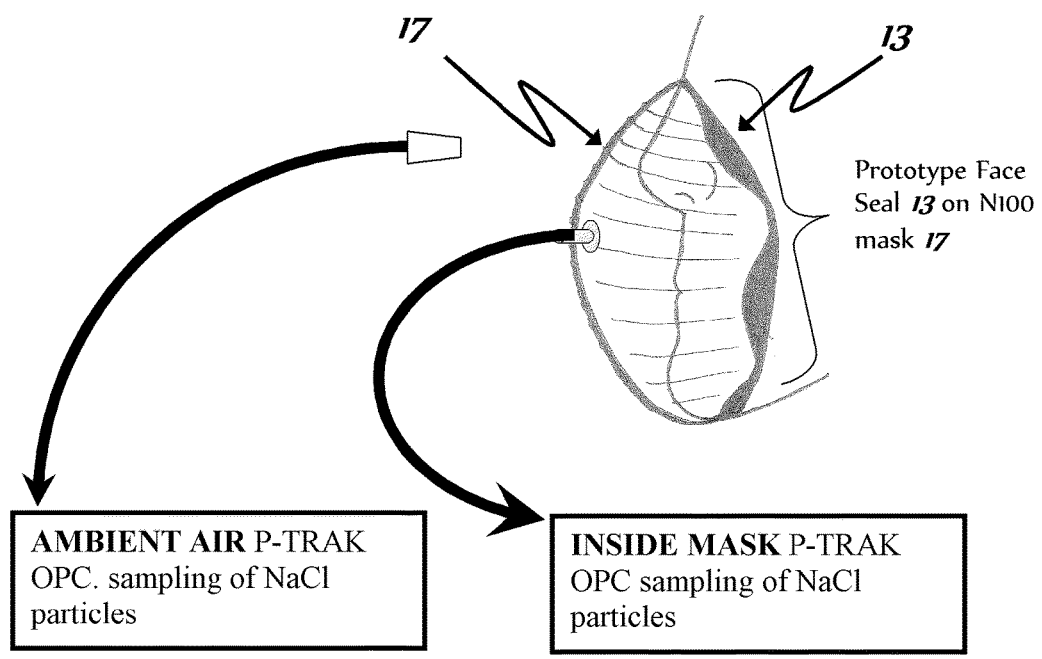
FIG. 6 demonstrates the experimental setup apparatus for initial laboratory FSIL studies, wherein is shown a stock N100 FFR mask 17 with the stock FS removed and replaced with the FS 13 attached.

FIG. 6 illustrates the laboratory test environment used, which has been widely described for research in the present state of the art (Balazy et al. 2006, Lee, et al, 2004, Choe et al 2000, Grinshpun et al. 2004, Lee et al 2008). A walk-in indoor test chamber (860 ft3=24.3 m3) was utilized to conduct the initial study. The test chamber was maintained at a positive pressure of 1 in. w.g. (249 Pa) during the experiments. Sodium chloride solution (NaCl, 1%, w/v) was aerosolized in the chamber by a six-hole collision nebulizer (BGI Inc., Waltham, Mass., USA) at a pressure of 20 psi ($1.38 \times 10^5$ Pa) and a flow rate of 12 l/min. Dry air was mixed with NaCl aerosols at a flow rate of 40 l/min. NaCl was used as a primary test aerosol at concentrations ranging from $4.2 \times 10^7$ to $1.9 \times 10^8$ particles/m3. Since laboratory-generated particles may carry high electrical charges, the entire airflow of 52 l/min was directed through a 10 mCi 85 Kr charge equilibrator (Model 3054, TSI, Inc., Minneapolis, Minn.,) to achieve the Boltzmann charge equilibrium. An air circulation fan (with a flow rate of 900 CFM) located at the outlet of the aerosol generation system distributed the aerosolized particles within the chamber.

In the initial experimental study, two different N100 FFR masks 17 were used, from two manufacturers that are both well recognized by those skilled in the art. Each FFR mask was tested in triplicate, in three versions: the first with the mask 17 stock FS in place; the second with the mask 17 FS removed and replaced with the FS 13 with a ¼ inch thickness affixed to the inside periphery of 17; the third with the stock FS of 17 removed and replaced with a FS 13 in a ⅜ inch thickness affixed to the inside periphery of mask 17. The exhalation valves on the masks 17 were left undisturbed.

In each of the modified prototypes tested, the FS 13 was heat-activated according the protocol as set forth above in FIG. 5.

Initially, the subject performed a user seal check as described in OSHA 29CFR1910. Part 1, Appendix A, Sec A, pp. 1-13. All subsequent experimental studies herein followed the above OSHA protocol, and all of the masks—controls and prototypes—passed the user seal check by all subjects.

A single human subject then performed the quantitative fit testing, which was conducted with a TSI P-TRAK (TSI, Inc., St. Paul, Minn., USA) optical particle counter (OPC), with customized software in order to obtain fit factors >200. Samples were obtained outside the mask (ambient air) and inside the mask via customized fittings placed centrally on the mask to which tubing connected the samples to separate OPC's.

Fit-testing exercises were performed according to the OSHA 29CFR1910.134, Part 1; Appendix A, Sec 14a "Test exercises", pp. 1-8. These exercises include normal breathing, deep breathing, turning the head from side to side, moving the head up and down, talking, grimace maneuver, bending over and touching the toes, and returning to normal breathing (US Department of Labor, 1998). Each exercise was performed for 2 min (versus OSHA's 1-min protocol) and the particle concentrations inside and outside the respirator were averaged over 1-min periods. The challenge NaCl aerosol concentrations were measured inside the Mask 17 and outside Mask 17.

The concentration inside the respirator (c-in) for the entire test was averaged over all the exercises, excluding the grimace maneuver. The particle concentrations outside the respirator (c-out) were measured at the beginning, middle and end of the test. The average of these concentrations was used as the concentration outside the respirator for each test. The FF was calculated by dividing the particle concentrations outside the respirator (c-out) by those inside the respirator (c-in): FF=c-out/c-in.

The particle losses in the sampling line have been addressed in previous studies (Lee et al., 2004). Therefore, all PFs presented in herein were corrected by a ratio of concentrations measured in the two sampling lines when no respirator was attached in the system. These ratios varied from 0.93 to 1, depending on the particle size.

The data analysis was performed using an analysis of variance (ANOVA) model provided by the Statistical Analysis System version 8.0 (SAS Institute Inc., Cary, N.C., USA). P-values of 0.05 were considered significant. The difference in mean FFs among nine surgical masks was examined by the ANOVA followed by a pairwise comparison using the Tukey's studentized range test. This statistical method was also used to examine the difference in the PFs among different particle sizes.

In all studies presented herein the FS 13 was composed of EVA foam (McMaster-Carr, Robbinsville, N.J.).

Study Results are presented herein:

Example 1

Figure 8:
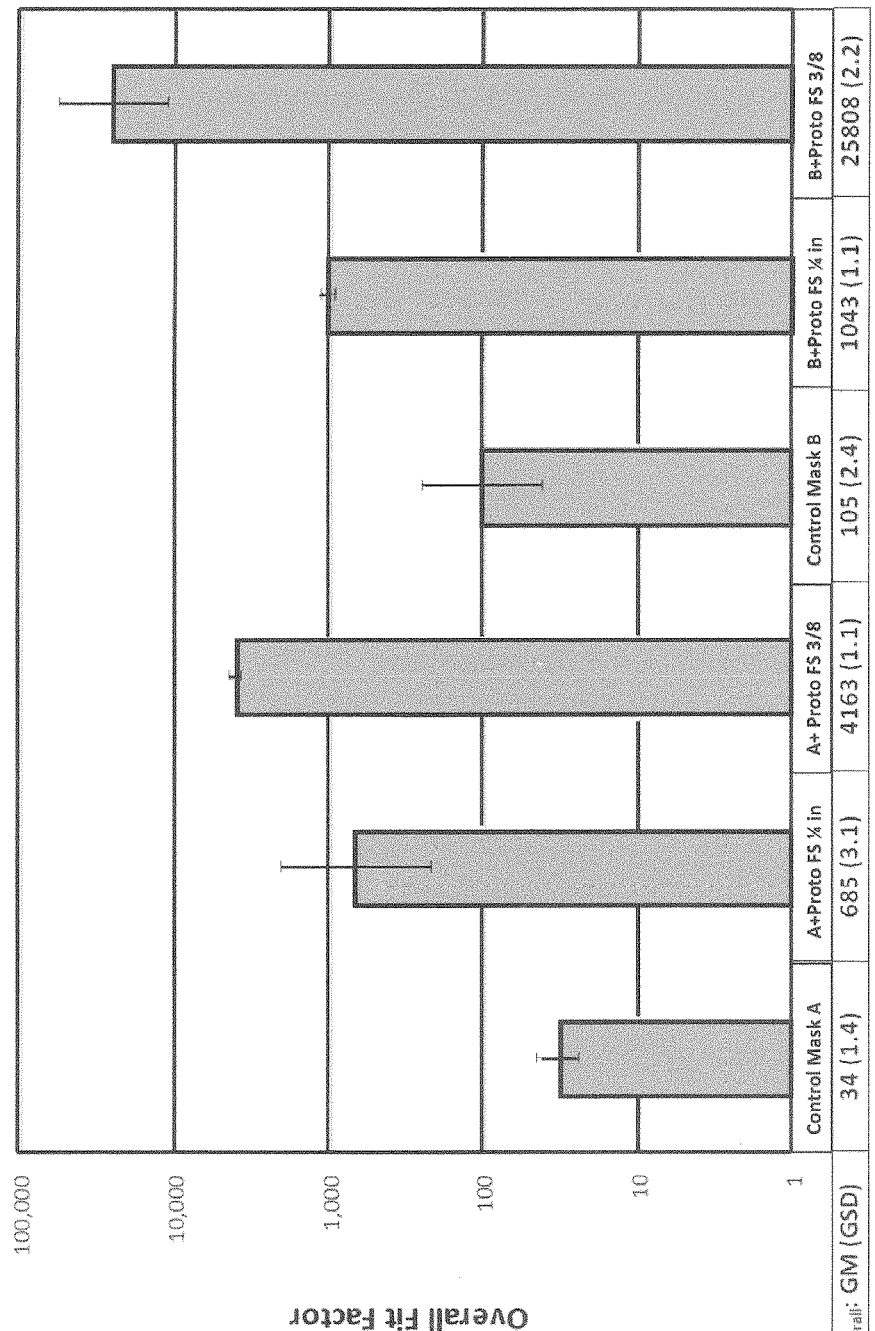
FIG. 8 is a graph depicting overall fit factors.

FIG. 8 represents results of the laboratory studies performed with the setup shown in FIG. 6, wherein: "Control-A"=Model A N100FFR mask with the stock FS; "[A+Proto¼FS]13"=Model A N100FFR mask modified with FS 13 having a ¼ in thickness; and "[A+Proto ⅜ FS]13"=Model A N100FFR mask modified with FS 13 having a ⅜ in thickness. The same labeling index applies to Control Model B N100FFR and all prototype versions of mask 17 thereof, and as described herein.

To make each prototype FFR, the Control FFR 17 stock FS was removed and the FS 13 was affixed to the inner periphery of mask 17 according to the protocol described in FIG. 5.

Among the two tested control N100 FFR respirators, Control-B performed better than the Control-A. In all three single fit tests, the overall fit factor (FFoverall) of the Control-A was below 100; for the Control-B, the FFoverall exhibited geometric mean (GM) slightly higher than the targeted OSHA threshold of 100. However, the difference between FFoverall-values of Control-A and Control-B showed a borderline statistical significance (p=0.06).

The [A+Proto¼FS]13 showed significant enhancement as compared to the Control-A with its stock FS: FFoverall GMs were 685 and 34, respectively; p=0.02. It should be acknowledged that the filter of any N100 respirator is expected to have a filtration efficiency of at least 99.97%, which could allow no more than 0.03% of particles to penetrate (one out of ~3,300), which translates to FFoverall >3,300. This means that, if such a respirator features FFoverall in excess of 3,300, the particle penetration may be attributed solely to the filter material, and not to FSIL; i.e., the respirator could be considered (in a first approximation) as "perfectly fit" (no room for the faceseal leakage). Given the difference between 685 and 3,300, [A+Proto¼FS]13 seems to have some degree of FSIL, although the modification with FS 13 improved the fit over the Control-A respirator by about 20-fold.

The [A+Proto⅜FS]13 showed an improved overall FF: over 100-fold greater than the non-modified Control-A and 6-fold greater than the previously tested [A+Proto¼FS]13. The level is not as high as [B+Proto⅜FS]13 (see below), but it's greater than 3,300 (min FF for the N100 filter), which suggests either no FSIL, or extremely small FSIL (with the leak penetration lower than or comparable to the filter penetration).

The [B+Proto¼FS]13 results were as follows: FFoverall showed both [B+Proto¼FS]13 and [B+Proto⅜FS]13 had considerable enhancement as compared to the Control-B: FFoverall GM-value that was 105 for control increased to 1,043 for [B+Proto¼FS]13 (significant difference: p=0.02) and to 25,808 for [B+Proto⅜FS]13 (significant difference: p<0.001). The overall fit factor of [B+Proto⅜FS]13 was 25-fold greater than the one for [B+Proto¼FS]13. The findings suggest that [B+Proto¼FS]13 still had at least some degree of FSIL (although much smaller than the Control-B) while [B+Proto⅜FS]13 seems "perfectly fit" (25,808>>3,300, i.e. no measurable faceseal leakage.

These results clearly prove that the FS 13, when affixed to both N100 FFR 17s Control-A and Control-B, resulted in highly significantly improved FFs for both of these FFRs. The results also indicated that both [B+Proto⅜FS]13 and [B+Proto¼FS]13 were much better than the corresponding versions of Control-A. For this reason, all subsequent studies presented herein utilized the Model-B N100 FFR since this model, in being able to demonstrate essentially no face seal leakage with FS 13, would provide the most accurate measurements of FS 13 performance in the SWPF and WPF studies as reported below.

Figure 7:
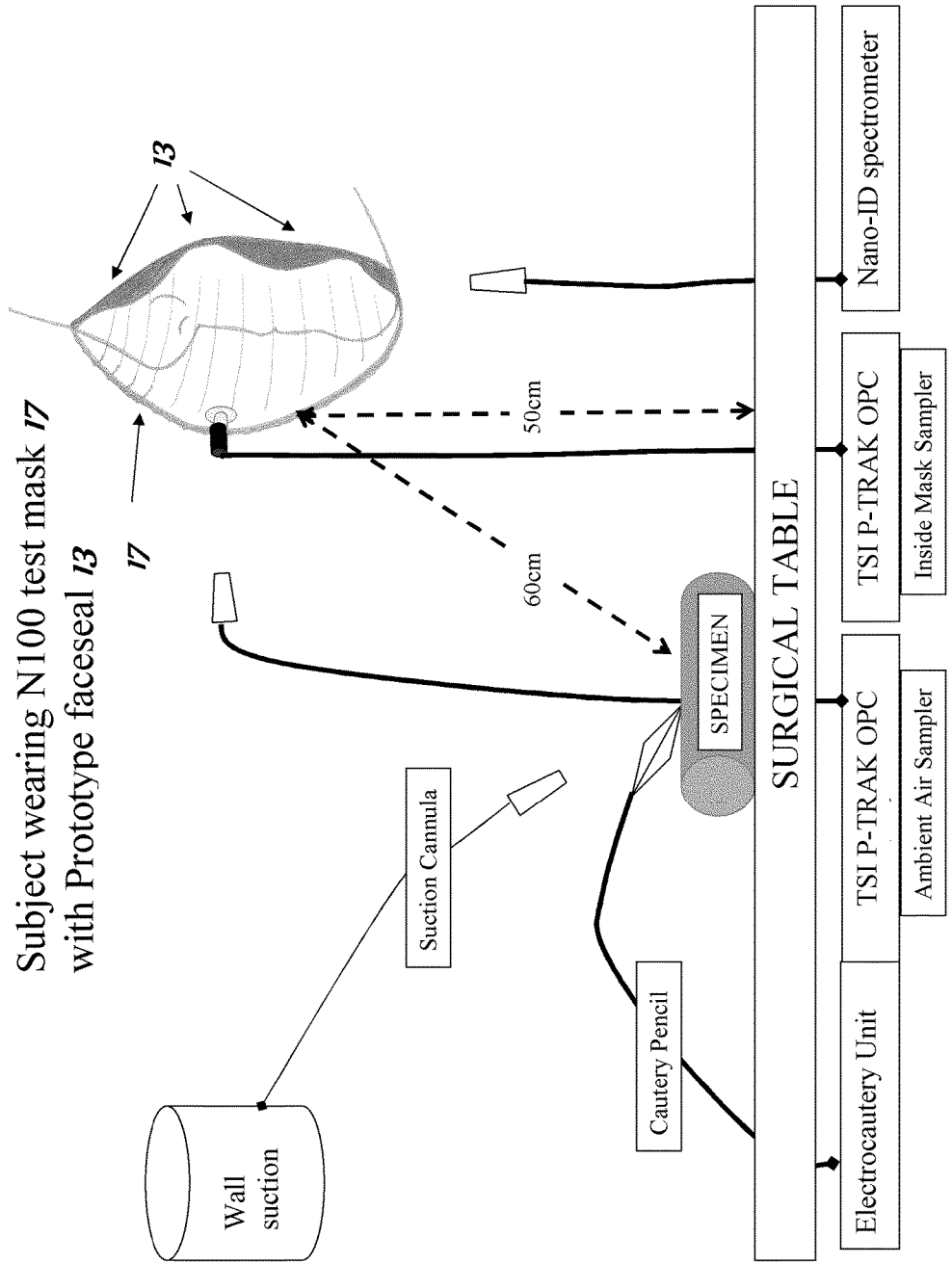
FIG. 7 demonstrates the experimental protocol for SWPF and WPF studies, using mask 17 with FS 13 in place.

FIG. 7 illustrates the setup for the Simulated Workplace Protective Factor (SWPF) study performed in a teaching university hospital surgical laboratory setting. The electrocautery smoke plume measurements were taken during an ongoing trauma surgery teaching exercise, being performed in a swine model, for the surgical residents in training. The training surgery exercise was approved by the institution's Investigational Review Board (IRB). The reason this is reported as a SWPF rather than a true Workplace Protective Factor (WPF) study design is solely because in this study setup, and unlike a true hospital operating room, there was no temperature and humidity control, and no negative air flow system. The rest of the study design would equate with that of a WPF study.

The study surgeon (an experienced board certified general surgeon) positioned himself at a customary distance from the surgical site. The electrosurgical generator unit (Valleylab Force FX, Covidien, Boulder, Colo.) was set at a blend current of 40 wts. A standard electrosurgical pencil (Valleylab E2516, Covidien, Boulder, Colo.) was used. The surgical smoke plume was suctioned at a customary distance by an experienced surgical assistant.

OPC placement, and tubing fixation to each mask tested, was identical to the protocol as shown in FIG. 6. The OPC measuring the ambient air was modified to be able to function with what proved to be extremely high particle counts in the surgical smoke plume. A ⅟₁₀ dilution was used when the ambient concentration was expected to be greater than 500,000 particles per cm3, which is the upper threshold of the P-TRAK.

The mask 17 used was identical to the Model-B N100 FFR as detailed in FIG. 6 above. The FS 13 was of the ⅜ in thickness for this study, and for all remaining study examples reported herein. Each version of the mask 17 was tested in triplicate: mask 17 with its stock FS; mask 17 with the stock FS removed and replaced with the FS 13 and not heated; mask 17 with the stock FS removed and replaced with the FS 13 and heated prior to use. Fixation of the FS 13 to the mask 17 was by the process detailed in FIG. 5. Heat activation of FS 13 was performed as detailed in FIG. 5, with the exception that the mask was held in place on the user's face, by the user, and the retaining straps placed and secured after, rather than before, the 90 second cooling period.

It should be noted: in this example and all subsequent study examples reported herein that:

the Model-B N100 FFR mask 17 was used, and in its unmodified state is herein referred to as "Control-B"

the FS 13 used was of the ⅜ in thickness version for this study, and for all of the remaining study examples presented, and is herein referred to as the "Prototype"

the Prototype with the FS 13 having been heated and fitted to user's face as described in FIG. 5 is herein referred to as the "HEATED Prototype"

the Prototype with the FS 13 in the non-heated version is referred to herein as the "NON-HEATED Prototype"

Study Results are presented herein:

Example 2

Figure 9:
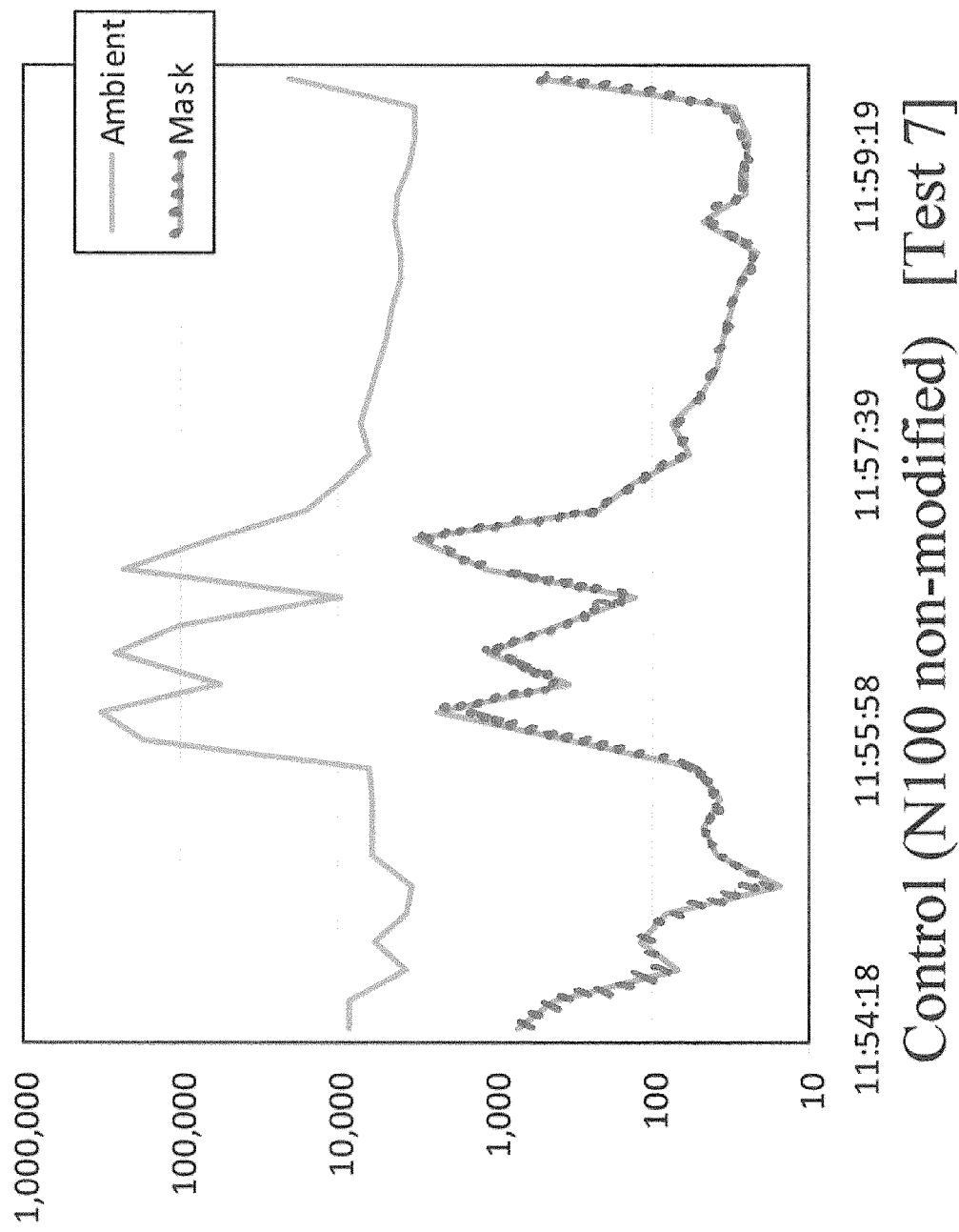
FIG. 9 is a graph depicting the results of SWPF studies.
Figure 10:
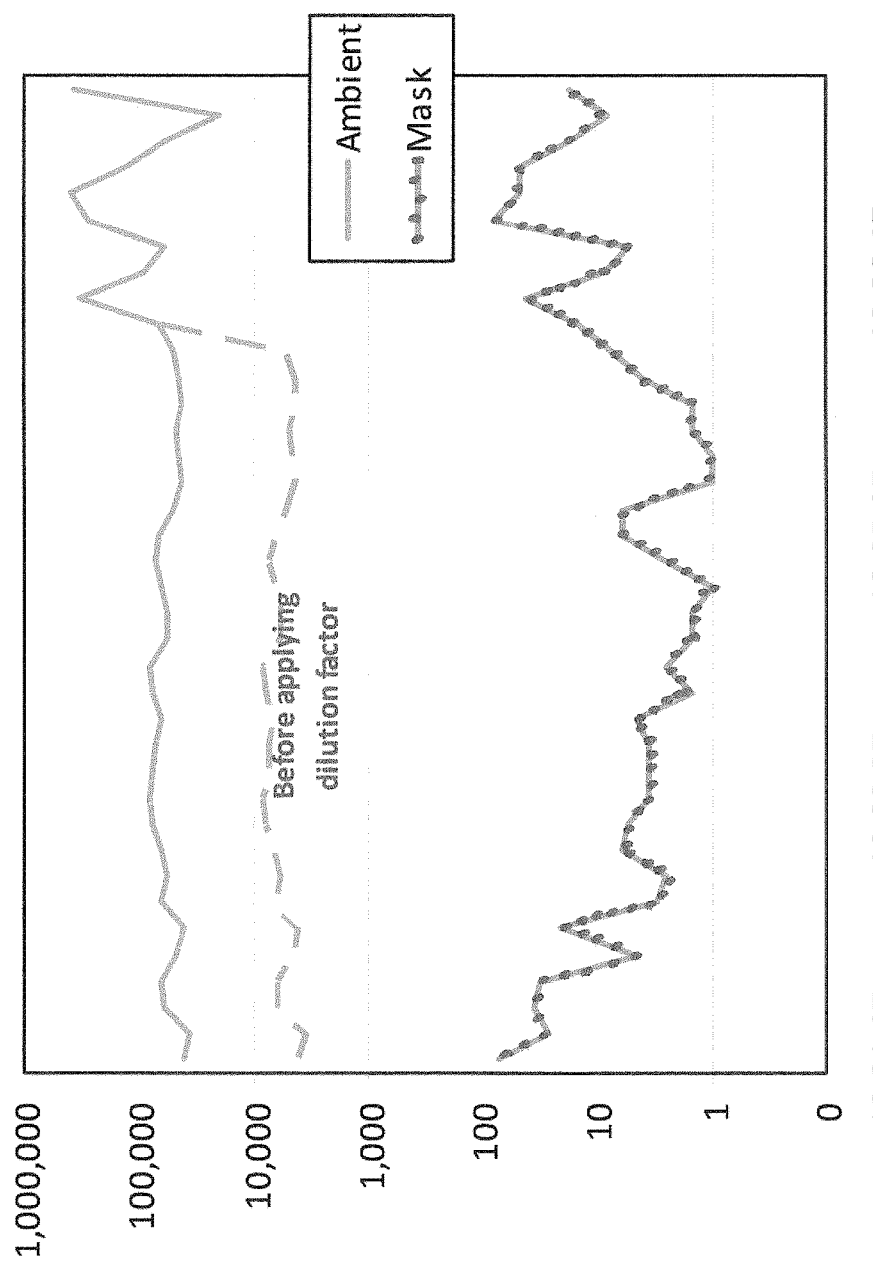
FIG. 10 is another graph depicting the results of SWPF studies.
Figure 11:
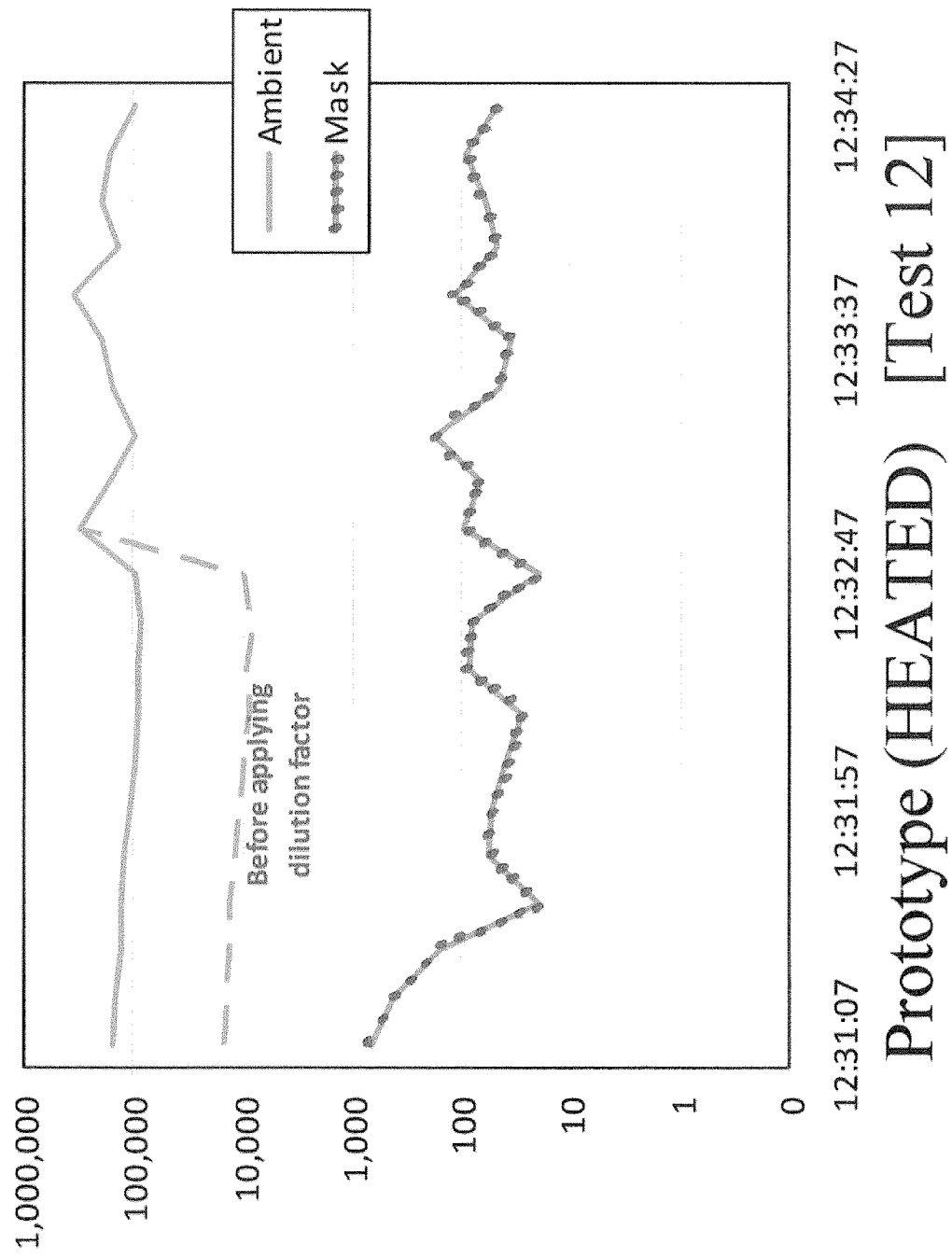
FIG. 11 is another graph depicting the results of SWPF studies.
Figure 12:
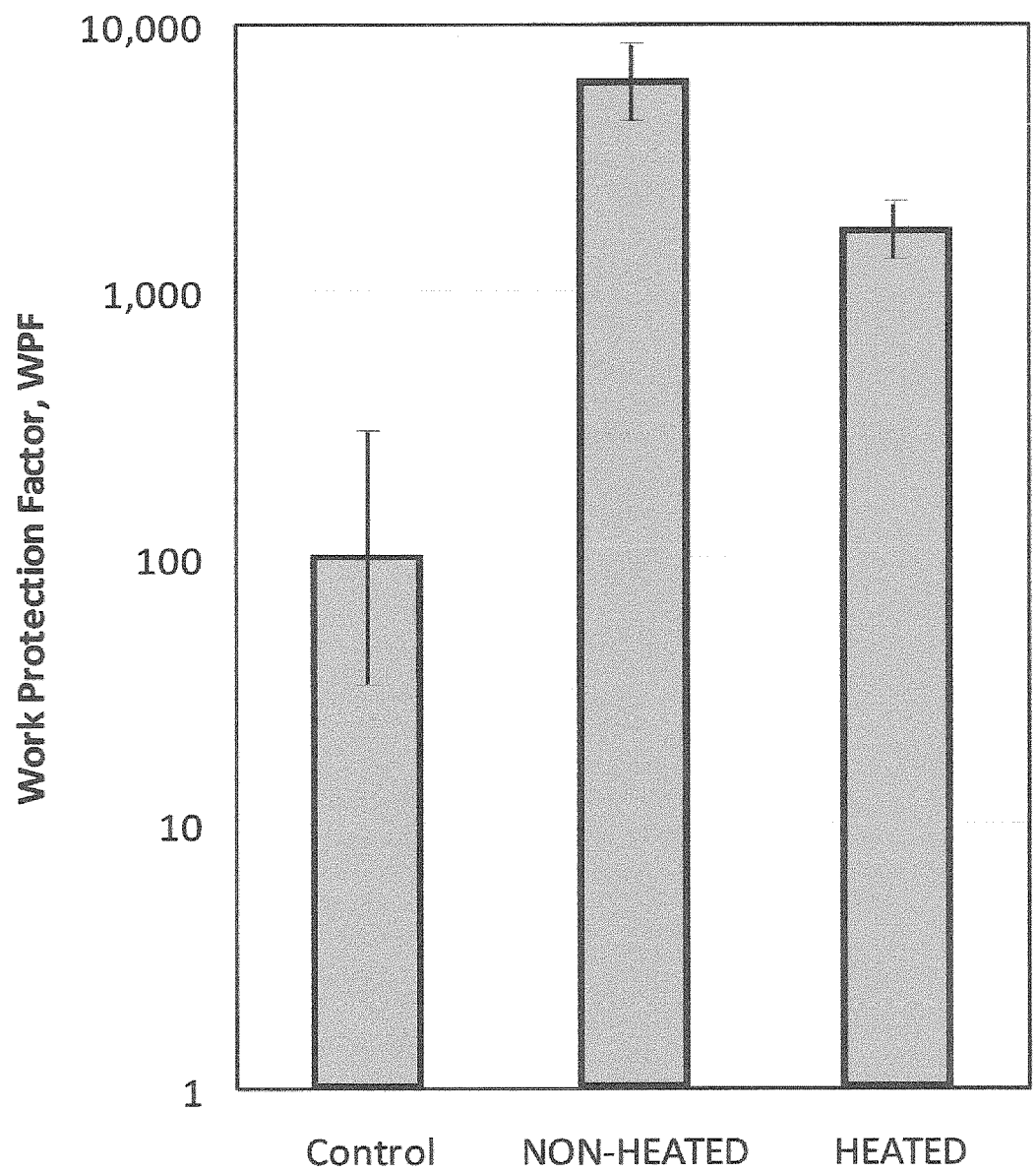
FIG. 12 is a chart depicting the WPF results of SWPF studies.

FIGS. 9-11 are results of the SWPF studies done as described in FIG. 7, and represent examples of the time series for the aerosol concentrations outside the respirator (ambient) and inside the respirator (mask) measured with a OPC in the operating room with the three study mask 17 versions: the Control-B; the NON-HEATED Prototype; the HEATED Prototype FIG. 12 represents SWPFs determined based on the OPC measurements in the operating room for the three mask 17 versions (the data from 12 tests were summarized). The bars represent GMs; the error bars represent standard deviations.

FIG. 13 represents numerical data for the SWPF values calculated using the time-weighted average concentration values for respirators 1, 4, 7, 10 (Control-B); 2, 8, 11 (NON-HEATED Prototype); and 3, 6, 9, 12, 13 (HEATED Prototype). The GMs and geometric standard deviations (GSD) are used in FIG. 12 above.

The SWPF of the NON-HEATED Prototypes was 61-fold higher than that for Control-B. This difference between GMs is statistically significant ($p=0.0081$). Four Control-B FFRs produced different SWPFs with 3 out of 4 above 100 and the GM-value close to 100. All three SWPFs produced by the NON-HEATED Prototypes were above 3,300 (the N100 filter can allow to penetrate 0.03% of particles which translates to (SWPF filter) min ~3,300; thus, any value in excess of 3,300 can technically represent a "perfectly fit" mask, i.e., the mask for which no measurable faceseal leakage was identified.

For the HEATED Prototypes, the SWPF was significantly higher than for the Control-B ($p=0.0032$), although it was not as high as for the NON-HEATED Prototypes (contrary to the expectations). The difference between the NON-HEATED Prototypes and the HEATED Prototype data sets was statistically significant ($p=0.0118$). The somewhat lower-than-expected performance of the HEATED Prototype was attributed to the leakage created due to the respirator re-donning (the following sequence was applied: heating, donning, taking off, re-donning). This part of the protocol deviated from the previous fit testing protocol as detailed in FIG. 5, and as used in FIG. 6, Example 1. It is believed that re-donning after, rather than before, the ninety (90) second cooling period described in FIG. 5 may not have allowed the user to achieve the same tight fit that was reached on the first donning with the respirator placed on the face immediately after heating as described in FIG. 5. It may be that certain deformations of the material aimed at mimicking the wearer's facial features may partially solidify between donnings, as the respirator cannot be positioned exactly the same, and FSIL leaks can be created near these deformations.

A measurable result of using the FS 13 as described herein, in both the NON-HEATED Prototypes and the HEATED Prototypes, is a more consistent performance: GSDs of both prototypes appeared considerably lower than the GSD for controls, as seen from FIG. 13. This result is significant in that the ambient concentration varied sizably (by two orders of magnitude in some tests).

Example 3

Figure 14:
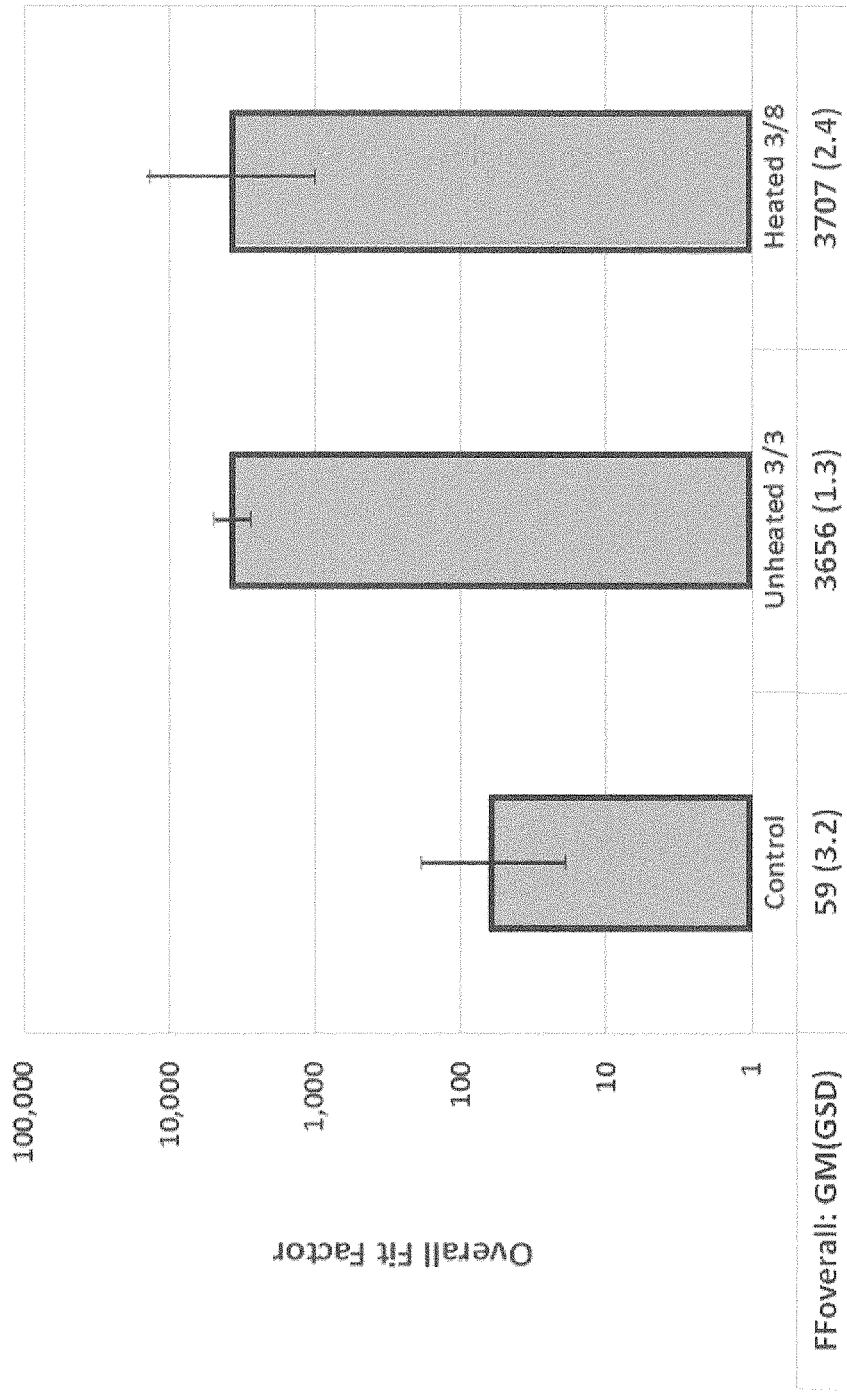
FIG. 14 is a chart depicting the overall fit factors from SWPF studies.

FIG. 14 represents an experimental study design with the same setup as seen in FIG. 6. and as reported in Example-1. The human subject was the same as that in Example-2 above, and hence different from Example-1. The same heating protocol for FS 13 as in Example-1 was utilized, as described in FIG. 5: after heating, the mask was placed to the face and straps secured, followed by the 90 second cooling period.

FIG. 15 represents the individual FFs for each mask as indicated in the Figure. Although the fit testing produced lower overall FFs than those obtained with the subject in Example-1, the protection levels obtained with the FS 13 prototypes were still very high. Both NON-HEATED Prototypes and HEATED Prototypes produced a FFoverall of approx. 3,700, which is (a) almost two order of magnitudes greater than the Control-B mask (GM=59), (b) above 3,300 that is assumed to be the filter-yielded threshold (which translates into "no measurable faceseal leak detected"). One of the HEATED Prototypes produced a FFoverall in excess of 10,000, which represents an absolute true "perfect fit".

The GM FFoverall of the HEATED and NON-HEATED Prototypes in this study are nearly identical, although the highest FFoverall was with the HEATED Prototype. The same subject in Example-2, with the same Control-B mask and the same Prototype Masks with FSs 13 had a greater difference in the GM FFoverall between the NON-HEATED Prototypes (higher) and the HEATED Prototypes (lower). The subject in Example-1, however, had significantly higher GM FFoveralls for the HEATED Prototypes than for the NON-HEATED Prototypes. These findings suggest that: a) the FS 13 functions best when heated and fitted as described in FIG. 5, and b) the HEATED and NON-HEATED Prototypes both substantially outperform the Control-B mask with its stock FS.

Example 4

This study setup was essentially the same as seen in Example 2, with three exceptions: 1) a section of animal tissue was used rather than a live animal; 2) the study took place in a fully functional hospital operating room with temperature and humidity controls as well as standard negative air flow; 3) three human study participants were used: the two participants involved in Example 1 and Example 2 & 3, and a third study participant. It should be noted that the anthropometrics of each participant's facial anatomy was significantly different, and that the first two participants were male and the third participant was female. Thus this study represented a true WPF design.

The OPC measuring the ambient air was modified to be able function with what proved to be extremely high particle counts in the surgical smoke plume. A 1/10 dilution was used when the ambient concentration was expected to be greater than 500,000 particles per cm3, which is the upper threshold of the P-TRAK.

A total of twenty seven tests were conducted: three with the Control-B, three with the NON-HEATED Prototype, and three with the HEATED Prototype. The heating protocol was used as described in FIG. 5, and as used in Examples 1 & 3 above. There were three subjects, three replicate tests per subject, and a randomized design was applied. For each test, a representative time segment was determined to compare the ambient and in-mask time-averaged aerosol concentrations taken from the time series (in most cases, a continuous monitoring period exceeded 1 min).

FIG. 16 represents individual mask's GMs and GSDs for each mask version tested.

Figure 17:
FIG. 17 is a chart depicting results of statistical analysis of SWPF study results.

FIG. 17 represents statistical analysis p-values for the Control-B masks as compared to the NON-HEATED and HEATED Prototypes.

Figure 18:
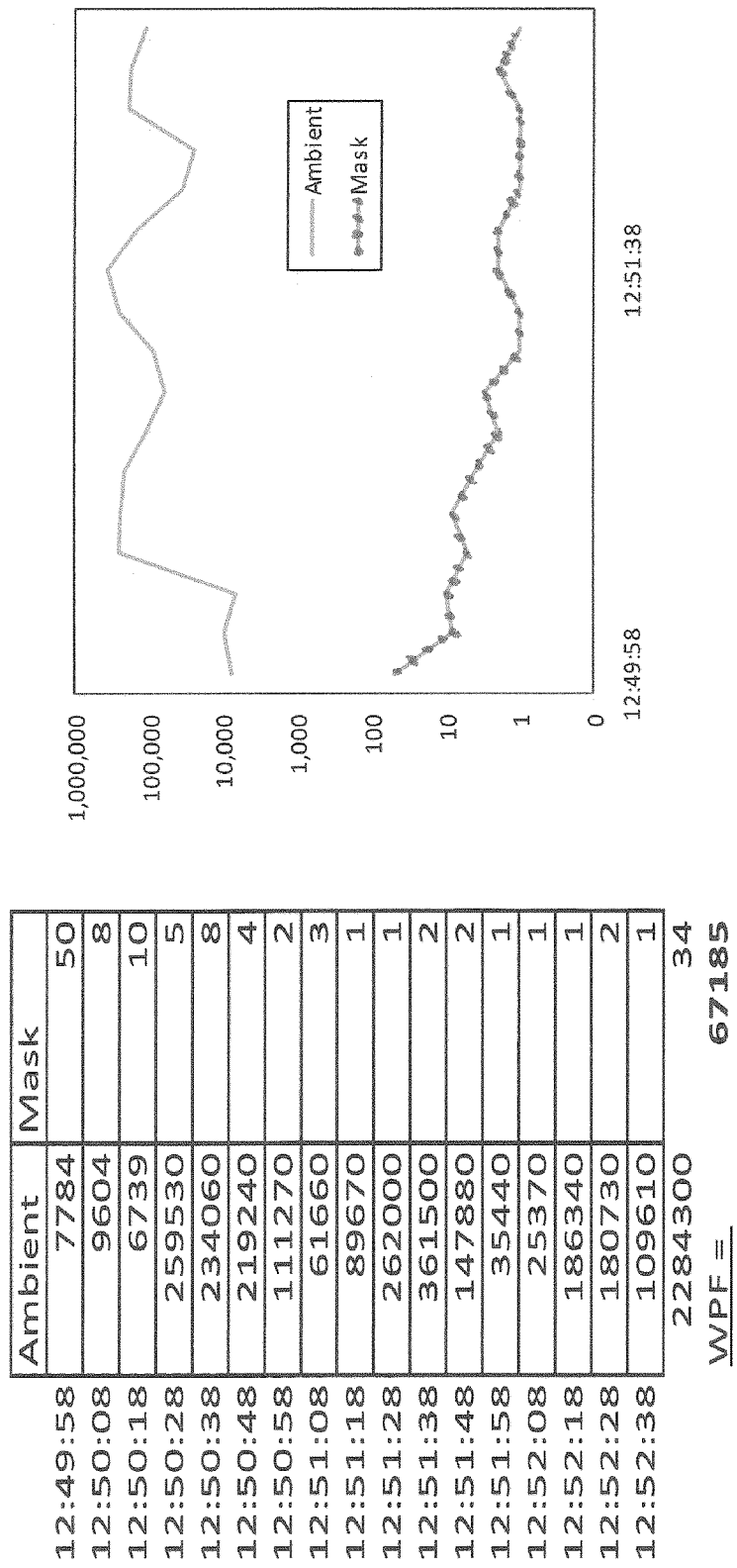
FIG. 18 is a chart depicting particle counts during SWPF studies.

FIG. 18 represents an example of the particle counts during the minute testing of a NON-HEATED Prototype mask, comparing ambient air counts versus inside mask counts.

Figure 19:
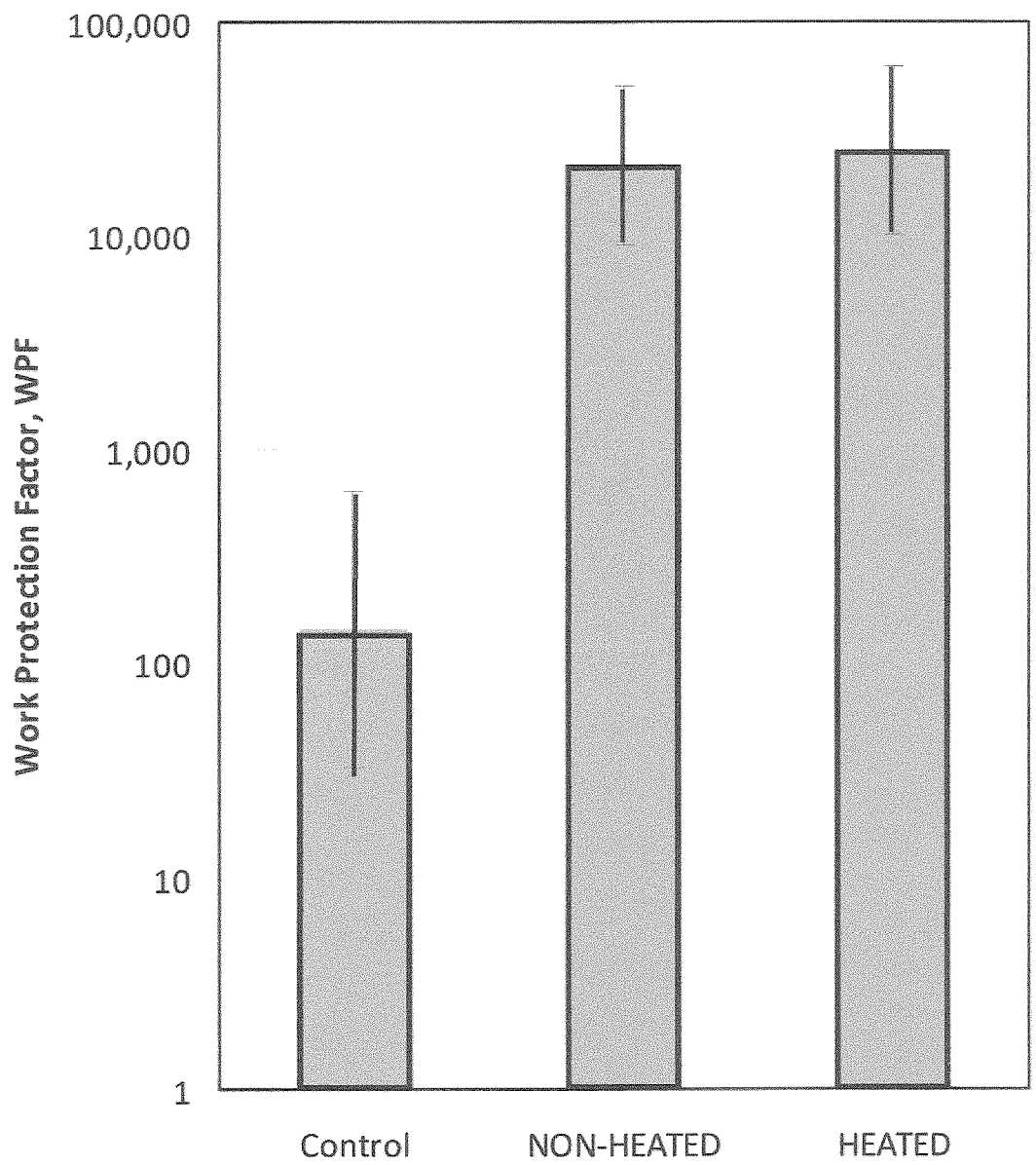
FIG. 19 is a chart depicting protection levels determined during SWPF studies.

FIG. 19 represents a graphical presentation of the protection level determined for the three respirator masks 17 versions—Control-B, NON-HEATED Prototype, and HEATED Prototype—as worn by the three subjects with three replicate tests per subject.

The findings indicate that no significant between-subject variability was observed in the performance of the Control-B mask and the NON-HEATED Prototype; the HEATED Prototype exhibited somewhat higher WPFs when tested on subjects SG and VA as compared to subject RK. The Control-B mask showed a proper fit only 5 times out of 9 (with WPF>100); it exhibited the WPF values ranging from 11.5 to 1,442 with GM of 145.6 and a GSD of 2.1.

The NON-HEATED Prototypes fitted all 9 times out of 9 (with WPF>>100); they exhibited WPF values ranging from 6,494 to 67,185 with a GM of 21,262 and a GSD of 1.5 (narrower, i.e. more consistent than the control model).

The HEATED Prototypes fitted all 9 times out of 9 (with WPF>>100); they exhibited WPF values ranging from 4,584 to 112,502 with a geometric mean GM of 24,923 and a GSD of 1.6.

The difference between WPFs of the Control-B Mask and either of the Prototypes (NON-HEATED or HEATED) is statistically significant (the strong significance is supported by $p<0.01$).

The GM of WPFs of the HEATED Prototype is about 15% greater than that of the NON-HEATED Prototype; however, this difference is not statistically significant ($p>0.05$). Thus, the two types of the FS 13 prototype FFRs exhibited similar performance characteristics (both demonstrated much superior protection levels than the Control B N100 Mask FFR.

While this invention has been described in connection with what are presently considered to be practical exemplary embodiments, it will be appreciated by those skilled in the art that various modifications and changes may be made without departing from the scope of the present disclosure. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Thus, while the present disclosure has described certain exemplary embodiments, it is to be understood that the invention is not limited to the disclosed embodiments, but, on the contrary, is intended to cover various modifications and equivalent arrangements included within the spirit and scope of the appended claims.

What is claimed is:

1. A face mask seal, comprising:
   a first surface;
   a second surface positioned opposite the first surface;
   an outer perimeter, the second surface or outer perimeter positioned for coupling to a face mask;
   an opening penetrating from the first surface to the second surface; and
   an inner perimeter having five convex and five concave accentuations, the inner perimeter completely surrounding the opening,
   two first convex accentuations of the five convex accentuations separated from each other by a first concave accentuation of the five concave accentuations,
   two second convex accentuations of the five convex accentuations separated from the first two convex accentuations by two second concave accentuations of the five concave accentuations, and
   a third convex accentuation of the five convex accentuations separated from the two second convex accentuations by two third concave accentuations of the five concave accentuations,
   the first two convex accentuations custom conforming to two first critical fit zones, respectively, on a user's face,
   the second two convex accentuations custom conforming to two second critical fit zones, respectively, on the user's face,
   the third convex accentuation custom conforming to a third critical fit zone on the user's face,
   the two first critical fit zones each including nasal bridge, nasomaxiliary ridge, maxillary zygomatic ridge, and a first portion of zygomatic process,
   the two second critical fit zones each including a second portion of the zygomatic process, bucchal wall soft tissues and a first portion of mandibular ramus, and
   the third critical fit zone including a second portion of the mandibular ramus on either side of submental soft tissues.

2. The face mask seal of claim 1, wherein the face mask seal is reusable.

3. The face mask seal of claim 1, wherein a distance between the first surface and the second surface is between about 1/16 inch and about 1/2 inch.

4. The face mask seal of claim 1, wherein the inner perimeter is formed of an elastomeric copolymer.

5. The face mask seal of claim 1, wherein the inner perimeter is formed of a thermoplastic elastomeric copolymer.

6. The face mask seal of claim 1, wherein the inner perimeter is formed of a thermoplastic copolymer.

7. The face mask seal of claim 6, wherein the thermoplastic copolymer is a foam.

8. The face mask seal of claim 6, wherein the thermoplastic copolymer is a solid.

9. The face mask seal of claim 1, wherein the inner perimeter comprises ethylene vinyl acetate (EVA).

10. The face mask seal of claim 9, wherein a distance between the first surface and the second surface is between about 1/16 inch and about 1/2 inch.

11. A face mask seal, comprising:
    a first surface;
    a second surface positioned opposite the first surface;

an outer perimeter, the second surface or outer perimeter positioned for coupling to a face mask;

an opening penetrating from the first surface to the second surface; and an inner perimeter having five convex and five concave accentuations, the inner perimeter completely surrounding the opening, two first convex accentuations of the five convex accentuations separated from each other by a first concave accentuation of the five concave accentuations, two second convex accentuations of the five convex accentuations separated from the first two convex accentuations by two second concave accentuations of the five concave accentuations, and a third convex accentuation of the five convex accentuations separated from the two second convex accentuations by two third concave accentuations of the five concave accentuations, the first two convex accentuations custom conforming to two first critical fit zones, respectively, on a user's face, the second two convex accentuations custom conforming to two second critical fit zones, respectively, on the user's face, the third convex accentuation custom conforming to a third critical fit zone on the user's face, the two first critical fit zones each including nasal bridge, nasomaxiliary ridge, maxillary zygomatic ridge, and a first portion of zygomatic process, the two second critical fit zones each including a second portion of the zygomatic process, bucchal wall soft tissues and a first portion of mandibular ramus, the third critical fit zone including a second portion of the mandibular ramus on either side of submental soft tissues, and the inner perimeter including one or more additional accentuations in a direction substantially perpendicular to either the first surface or the second surface and substantially perpendicular to the five convex and the five concave accentuations.

12. The face mask seal of claim 11, wherein the face mask seal is reusable.

13. The face mask seal of claim 11, wherein a distance between the first surface and the second surface is between about 1/16 inch and about 1/2 inch.

14. The face mask seal of claim 11, wherein the inner perimeter is formed of an elastomeric copolymer.

15. The face mask seal of claim 11, wherein the inner perimeter is formed of a thermoplastic elastomeric copolymer.

16. The face mask seal of claim 11, wherein the inner perimeter is formed of a thermoplastic copolymer.

17. The face mask seal of claim 16, wherein the thermoplastic copolymer is a foam.

18. The face mask seal of claim 16, wherein the thermoplastic copolymer is a solid.

19. The face mask seal of claim 11, wherein the inner perimeter comprises ethylene vinyl acetate (EVA).

20. The face mask seal of claim 19, wherein a distance between the first surface and the second surface is between about 1/16 inch and about 1/2 inch.

* * * * *